(12) United States Patent
Boehringer et al.

(10) Patent No.: US 6,867,205 B2
(45) Date of Patent: Mar. 15, 2005

(54) PYRIDINE AND PYRIMIDINE DERIVATIVES

(75) Inventors: Markus Boehringer, Moehlin (CH); Bernd Michael Loeffler, Oberrimsingen (DE); Jens-Uwe Peters, Grenzach-Wyhlen (DE); Matthias Steger, Zurich (CH); Peter Weiss, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/361,268

(22) Filed: Feb. 10, 2003

(65) Prior Publication Data

US 2003/0216382 A1 Nov. 20, 2003

(30) Foreign Application Priority Data

Feb. 13, 2002 (EP) ............................................ 02003114

(51) Int. Cl.[7] .................... C07D 239/42; C07D 401/04; A61K 31/505
(52) U.S. Cl. .............................. 514/217.06; 514/235.8; 514/256; 514/269; 514/275; 544/122; 544/317; 544/323; 544/326; 544/328
(58) Field of Search ................................ 544/122, 317, 544/323, 326, 328; 540/601; 514/217.06, 256, 235.8, 269, 275

(56) References Cited

U.S. PATENT DOCUMENTS

| | | | | |
|---|---|---|---|---|
| 6,011,155 A | 1/2000 | Villhauer | .................... | 514/333 |
| 6,110,949 A | 8/2000 | Villhauer | .................... | 514/365 |
| 6,303,661 B1 | 10/2001 | Demuth et al. | ............. | 548/866 |
| 6,319,893 B1 | 11/2001 | Demuth et al. | ................ | 514/2 |

FOREIGN PATENT DOCUMENTS

| | | |
|---|---|---|
| DE | 196 16 486 | 10/1997 |
| DE | 198 34 591 | 2/2000 |
| WO | WO 98/19998 | 5/1998 |
| WO | WO 99/38501 | 8/1999 |
| WO | WO 00/34241 | 6/2000 |
| WO | WO 00 61562 | 10/2000 |
| WO | WO 01/40180 | 6/2001 |
| WO | WO 01/55105 | 8/2001 |
| WO | WO 01 64679 | 9/2001 |
| WO | WO 01/96295 | 12/2001 |

OTHER PUBLICATIONS

Clark, Understanding and managing treatment, Understanding Diabetes, pp. 67–71, 2004.*

Nagakura et al., PubMed Abstract (Metabolism. 52(1):81–6), Jan. 2003.*

Pospisilik et al., Dipeptidyl Peptidase IV Inhibitor Treatment Stimulates beta–cell Survival and Islet Neogenesis in Streptozotocin–Induced Diabetic Rats, Diabetes, vol. 52, pp. 741–750, Mar. 2003.*

Perandones et al., Synthesis of Pyrido[2,3]pyrimidines from Aminopyrimidinecarbaldehydes, J. Heterocyclic Chem. 35, pp. 413–419, Mar.–Apr., 1998.*

* cited by examiner

Primary Examiner—Deepak Rao
(74) Attorney, Agent, or Firm—George W. Johnston; Dennis P. Tramaloni; Samuel H. Megerditchian

(57) ABSTRACT

The present invention provides compounds of formula (I)

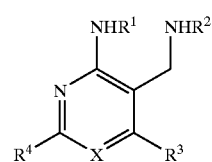

wherein $R^1$, $R^2$, $R^3$, $R^4$ and X are as defined in the specification, and pharmaceutically acceptable salts thereof. The compounds are useful for the treatment and/or prophylaxis of diseases which are associated with DPP IV, such as diabetes, particularly non-insulin dependent diabetes mellitus, and impaired glucose tolerance.

18 Claims, No Drawings

PYRIDINE AND PYRIMIDINE DERIVATIVES

BACKGROUND OF THE INVENTION

The enzyme dipeptidyl peptidase IV (EC.3.4.14.5, abbreviated in the following as DPP-IV) is involved in the regulation of the activities of several hormones. In particular, DPP-IV efficiently and rapidly degrades glucagon-like peptide 1 (GLP-1), which is one of the most potent stimulators of insulin production and secretion. Inhibiting DPP-IV would potentiate the effect of endogenous GLP-1, and lead to higher plasma insulin concentrations. In patients suffering from impaired glucose tolerance and type 2 diabetes mellitus, higher plasma insulin concentration would moderate the dangerous hyperglycaemia and accordingly reduce the risk of tissue damage. Consequently, DPP-IV inhibitors have been suggested as drug candidates for the treatment of impaired glucose tolerance and type 2 diabetes mellitus (e.g. Vilhauer, WO98/19998). Other related state of the art can be found in WO 99/38501, DE 19616486, DE 19834591, WO 01/40180, WO 01/55105, U.S. Pat. No. 6,110,949, WO 00/34241 and U.S. Pat. No. 6,011,155.

SUMMARY OF THE INVENTION

The present invention provides compounds of the formula (I)

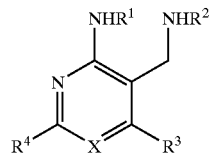

wherein
x is N or C—$R^5$;
$R^1$ and $R^2$ are independently hydrogen or lower alkyl;
$R^3$ is heterocyclyl; heterocyclyl mono-, di-, or tri-substituted, independently, by lower alkyl, perfluoro-lower alkyl, amino, lower alkoxy or halogen; aryl; or aryl mono-, di-, or tri-substituted, independently, by halogen, lower alkyl, amino, lower alkoxy or perfluoro-lower alkyl;
$R^4$ is lower alkyl; lower alkoxy; lower alkylthio; heterocyclyl; heterocyclyl mono-, di-, or tri-substituted, independently, by lower alkyl, lower alkoxy, perfluoro-lower alkyl, amino or halogen; aryl; aryl mono-, di-, or tri-substituted, independently, by lower alkyl, lower alkoxy, halogen, amino, or perfluoro-lower alkyl; aryloxy lower alkyl or cycloalkyl;
$R^5$ is hydrogen or lower alkyl; and pharmaceutically acceptable salts thereof.

DETAILED DESCRIPTION OF THE INVENTION

We have found novel DPP-IV inhibitors that very efficiently lower plasma glucose levels. Consequently, the compounds of the present invention are useful for the treatment and/or prophylaxis of diabetes, particularly non-insulin dependent diabetes mellitus, and/or impaired glucose tolerance, as well as other conditions wherein the amplification of action of a peptide normally inactivated by DPP-IV gives a therapeutic benefit. Surprisingly, the compounds of the present invention can also be used in the treatment and/or prophylaxis of obesity Bowl disease, Colitis Ulcerosa, Morbus Crohn, and/or metabolic syndrome. Furthermore, the compounds of the present invention can be used as diuretic agents and for the treatment and/or prophylaxis of hypertension. Unexpectedly, the compounds of the present invention exhibit improved therapeutic and pharmacological properties compared to other DPP IV inhibitors known in the art, such as e.g. in context with pharmacokinetics and bioavailability.

The present invention provides compounds of the formula (I)

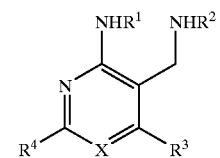

wherein
X is N or C—$R^5$;
$R^1$ and $R^2$ are independently hydrogen or lower alkyl;
$R^3$ is heterocyclyl; heterocyclyl mono-, di-, or tri-substituted, independently, by lower alkyl, perfluoro-lower alkyl, amino, lower alkoxy or halogen; aryl; or aryl mono-, di-, or tri-substituted, independently, by halogen, lower alkyl, amino, lower alkoxy or perfluoro-lower alkyl;
$R^4$ is lower alkyl; lower alkoxy; lower alkylthio; heterocyclyl; heterocyclyl mono-, di-, or tri-substituted, independently, by lower alkyl, lower alkoxy, perfluoro-lower alkyl, amino or halogen; aryl; aryl mono-, di-, or tri-substituted, independently, by lower alkyl, lower alkoxy, halogen, amino, or perfluoro-lower alkyl; aryloxy lower alkyl or cycloalkyl;
$R^5$ is hydrogen or lower alkyl;
and pharmaceutically acceptable salts thereof.

Unless otherwise indicated, the following definitions are set forth to illustrate and define the meaning and scope of the various terms used to describe the invention herein.

In this specification the term "lower" is used to mean a group consisting of one to six, preferably of one to four carbon atom(s).

The term "halogen" refers to fluorine, chlorine, bromine and iodine, with fluorine, bromine and chlorine being preferred. Most preferred halogen is chlorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred.

The term "perfluoro-lower alkyl" refers to a lower alkyl group wherein all of the hydrogens of the lower alkyl group are substituted or replaced by fluoro. Among the preferred perfluoro-lower alkyl groups are trifluoromethyl, pentafluoroethyl and heptafluoropropyl, with trifluoromethyl being especially preferred.

The term "alkoxy" refers to the group R'—O—, wherein R' is alkyl. The term "lower-alkoxy" refers to the group R"—O—, wherein R" is lower-alkyl. Examples of lower alkoxy groups are e.g. methoxy, ethoxy, propoxy, isopropoxy, butoxy, isobutoxy and hexyloxy, with methoxy being especially preferred.

The term "lower alkylthio" refers to the group R'—S—, wherein R' is lower-alkyl as defined above.

The term "cycloalkyl" refers to a monovalent carbocyclic radical of three to six, preferably three to five carbon atoms. This term is further exemplified by radicals such as cyclopropyl, cyclobutyl, cyclopentyl and cyclohexyl, with cyclopropyl being preferred.

The term "heterocyclyl" refers to a saturated, unsaturated or aromatic monovalent 5- to 7-membered monocyclic, 9-membered bicyclic or 13-membered tricyclic radical having at least one heteroatom selected from nitrogen, sulfur and oxygen, for example, containing a combination of any of such heteroatoms. Examples of heterocyclyl residues are pyridyl, pyrimidinyl, furyl, thienyl, indolyl, benzo[1,3]dioxolyl, benzofuranyl, benzothiophenyl, dibenzofuranyl, oxazolyl, imidazolyl, thiazolyl, isoxazolyl, pyrazolyl, isothiazolyl, oxadiazolyl, thiadiazolyl, triazolyl, tetrazolyl, oxatriazolyl, thiatriazolyl, pyridazyl, pyrimidinyl, pyrazinyl, pyrrolidinyl, azepanyl, and morpholino. Substituted heterocyclyl residues are heterocyclyl which is mono-, di- or tri-substituted, independently, by halogen, amino, perfluoro-lower alkyl, lower alkyl or lower alkoxy, preferably by lower alkyl or lower alkoxy.

The term "aryl" refers to an aromatic monovalent mono- or polycarbocyclic radical, such as phenyl and naphthyl, preferably phenyl. Substituted aryl is aryl which is mono-, di- or tri-substituted, independently, by lower alkyl, lower alkoxy, halogen, amino or perfluoro-lower alkyl, preferably by lower alkyl, lower alkoxy and halogen.

The term "aryloxy lower alky" refers to an aryl residue as defined above attached to a lower alkylene group via an oxy radical, i.e. aryl-O—R, wherein R is lower alkylene.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In one embodiment of the present invention, $R^1$ is lower alkyl, with methyl and isopropyl being preferred. In a preferable embodiment, $R^1$ is hydrogen.

In another embodiment of the present invention, $R^2$ is lower alkyl, with methyl being preferred. In a preferable embodiment, $R^2$ is hydrogen.

In one embodiment of the present invention, X is N. In another embodiment, X is C—$R^5$. Preferable X is N.

In one embodiment, $R^3$ is heterocyclyl, such as pyridyl, pyrimidinyl, furyl, thienyl, indolyl, benzo[1,3]dioxolyl, benzofuranyl, benzothiophenyl, dibenzofuranyl, oxazolyl, imidazolyl, thiazolyl, isoxazolyl, pyrazolyl, isothiazolyl, oxadiazolyl, thiadiazolyl, triazolyl, tetrazolyl, oxatriazolyl, thiatriazolyl, pyridazyl, pyrazinyl, pyrrolidinyl, azepanyl and morpholino. Substituted heterocyclyl residues are mono-, di- or tri-substituted, independently, by lower alkyl, lower alkoxy, perfluoro-lower alkyl, amino or halogen, preferably by lower alkyl, lower alkoxy or halogen. Preferred heterocyclyl residues $R^3$ are unsubstituted thienyl and unsubstituted benzo[1,3]dioxolyl.

In a preferable embodiment, $R^3$ is aryl, preferably phenyl, optionally ortho-, meta- and/or para-, preferably ortho- and para-substituted, independently, by lower alkyl, lower alkoxy, halogen, amino or perfluoro-lower alkyl, preferably by halogen, lower alkyl, perfluoro-lower alkyl or lower alkoxy. Most preferable residue $R^3$ is 2,4-dichloro-phenyl.

In one embodiment, $R^4$ is aryl such as phenyl or naphthyl, with phenyl being preferred. Phenyl residues $R^4$ may optionally be ortho-, meta- and/or para-substituted, independently, by halogen, amino, lower alkyl, perfluoro-lower alkyl or lower alkoxy, preferably by halogen, such as fluoro, by lower alkyl, such as methyl or lower alkoxy, such as methoxy. Naphthyl residues $R^4$ are preferably unsubstituted or mono-substituted by lower alkoxy, such as methoxy.

In another embodiment $R^4$ is lower alkoxy, preferably methoxy. In still another embodiment $R^4$ is lower alkyl. Preferable lower alkyl residues $R^4$ are methyl and isopropyl. In another embodiment $R^4$ is cycloalkyl, with cyclopropyl being preferred. In another embodiment $R^4$ is lower alkylthio, preferably methylthio.

In another embodiment $R^4$ is heterocyclyl. Preferable heterocyclyl residues $R^4$ are pyridyl, pyrimidinyl, furyl, thienyl, indolyl, benzo[1,3]dioxolyl, benzofuranyl, benzothiophenyl, dibenzofuranyl, oxazolyl, imidazolyl, thiazolyl, isoxazolyl, pyrazolyl, isothiazolyl, oxadiazolyl, thiadiazolyl, triazolyl, tetrazolyl, oxatriazolyl, thiatriazolyl, pyridazyl, pyrimidinyl, pyrazinyl, pyrrolidinyl, azepanyl, and morpholino. More preferable are pyridyl, thienyl, indolyl, benzo[1,3]dioxolyl, benzofuranyl, benzothiophenyl, dibenzofuranyl, pyrrolidinyl, azepanyl and morpholino. Preferable substituted heterocyclyl residues are the preferable heterocyclyl residues mentioned and which are mono-, di- or tri-substituted, preferably mono- or di-substituted, independently, by halogen, amino, perfluoro-lower alkyl, lower alkyl or lower alkoxy, preferably by lower alkyl or lower alkoxy.

In still another embodiment, $R^4$ is aryloxy lower alkyl. Preferable aryloxy lower alkyl is phenoxy lower alkyl, wherein the phenyl moiety is substituted by halogen. Most preferable aryloxy lower alkyl is 4-fluorophenoxymethyl.

In one embodiment of the present invention, $R^5$ is lower alkyl, with methyl being preferred. In another embodiment, $R^5$ is hydrogen.

Preferred compounds in accordance with the present invention are those compounds of formula I, wherein X is N, $R^1$ and $R^2$ are hydrogen, $R^3$ is an aryl or substituted aryl residue as defined above, preferably a phenyl residue which is ortho- and para-substituted, independently, by lower alkyl, lower alkoxy, halogen, amino or perfluoro-lower alkyl, most preferably 2,4-dichloro-phenyl, and $R^4$ is alkoxy, preferably methoxy, alkylthio, preferably methylthio, aryl, preferably a phenyl or substituted phenyl residue which is ortho-, meta- and/or para-substituted, independently, as defined above, preferably by halogen, such as fluoro, by lower alkyl, such as methyl or lower alkoxy, such as methoxy, or a heterocyclyl or substituted heterocyclyl residue as defined above, preferably pyrrolidinyl or azepanyl.

Preferred compounds of general formula (I) are those selected from the group consisting of:

5-Aminomethyl-6-(2,4-dichloro-phenyl)-2-phenyl-pyrimidin-4-ylamine,

5-Aminomethyl-2-phenyl-6-p-tolyl-pyrimidin-4-ylamine,

5-Aminomethyl-6-(2,4-dichloro-phenyl)-2-(3-methoxy-phenyl)-pyrimidin-4-ylamine,

5-Aminomethyl-2-phenyl-6-o-tolyl-pyrimidin-4-ylamine,

5-Aminomethyl-6-(2,4-difluoro-phenyl)-2-phenyl-pyrimidin-4-ylamine,

5-Aminomethyl-6-(2,4-dichloro-phenyl)-2-m-tolyl-pyrimidin-4-ylamine,
5-Aminomethyl-6-(2,4-dichloro-phenyl)-2-(3,4,5-trimethoxy-phenyl)-pyrimidin-4-ylamine,
5-Aminomethyl-6-(2,4-dimethyl-phenyl)-2-phenyl-pyrimidin-4-ylamine,
5-Aminomethyl-6-(2,4-dichloro-phenyl)-2-(3,5-dimethoxy-phenyl)-pyrimidin-4-ylamine,
5-Aminomethyl-6-(2,4-dichloro-phenyl)-2-(3-fluoro-phenyl)-pyrimidin-4-ylamine,
5-Aminomethyl-6-(2,4-dichloro-phenyl)-2-(4-fluoro-phenyl)-pyrimidin-4-ylamine,
5-Aminomethyl-6-(2,4-dichloro-phenyl)-2-(4-methoxy-1-methyl-1H-indol-6-yl)-pyrimidin-4-ylamine,
5-Aminomethyl-2-benzofuran-2-yl-6-(2,4-dichloro-phenyl)-pyrimidin-4-ylamine,
5-Aminomethyl-6-(2,4-dichloro-phenyl)-2-(1H-indol-2-yl)-pyrimidin-4-ylamine,
5-Aminomethyl-6-(2,4-dichloro-phenyl)-2-m-tolyl-pyrimidin-4-ylamine,
2-(4-Amino-3-methoxy-phenyl)-5-aminomethyl-6-(2,4-dichloro-phenyl)-pyrimidin-4-ylamine,
5-Aminomethyl-2-azepan-1-yl-6-(2,4-dichloro-phenyl)-pyrimidin-4-ylamine,
5-Aminomethyl-6-(2,4-dichloro-phenyl)-2-(3,4-difluoro-phenyl)-pyrimidin-4-ylamine,
5-Aminomethyl-6-(2,4-dichloro-phenyl)-2-pyrrolidin-1-yl-pyrimidin-4-ylamine,
5-Aminomethyl-6-(2,4-dichloro-phenyl)-2-methylsulfanyl-pyrimidin-4-ylamine,
5-Aminomethyl-6-(2,4-dichloro-phenyl)-2-(3,4-dimethoxy-phenyl)-pyrimidin-4-ylamine,
5-Aminomethyl-6-(2,4-dichloro-phenyl)-2-thiophen-2-yl-pyrimidin-4-ylamine,
5-Aminomethyl-6-(2,4-dichloro-phenyl)-2-(2-fluoro-phenyl)-pyrimidin-4-ylamine,
5-Aminomethyl-2-(4-chloro-phenyl)-6-(2,4-dichloro-phenyl)-pyrimidin-4-ylamine,
5-Aminomethyl-6-(2,4-dichloro-phenyl)-2-methoxy-pyrimidin-4-ylamine,
5-Aminomethyl-2-cyclopropyl-6-phenyl-pyrimidin-4-ylamine5-Aminomethyl-6-(2,4-dichloro-phenyl)-2-p-tolyl-pyrimidin-4-ylamine,
5-Aminomethyl-6-(2,4-dichloro-phenyl)-2-(4-methoxy-phenyl)-pyrimidin-4-ylamine,
5-Aminomethyl-2-benzo[1,3]dioxol-5-yl-6-(2,4-dichloro-phenyl)-pyrimidin-4-ylamine,
5-Aminomethyl-6-(2,4-dichloro-phenyl)-2-(3-trifluoromethyl-phenyl)-pyrimidin-4-ylamine,
5-Aminomethyl-6-(2,4-dichloro-phenyl)-2-morpholin-4-yl-pyrimidin-4-ylamine,
5-Aminomethyl-6-(2,4-dichloro-phenyl)-2-(4-trifluoromethyl-phenyl)-pyrimidin-4-ylamine,
5-Aminomethyl-2-(3-chloro-phenyl)-6-(2,4-dichloro-phenyl)-pyrimidin-4-ylamine,
5-Aminomethyl-6-(2,4-dichloro-phenyl)-2-methyl-pyrimidin-4-ylamine,
5-Aminomethyl-6-(2,4-dichloro-phenyl)-2-naphthalen-2-yl-pyrimidin-4-ylamine,
5-Aminomethyl-6-(2,4-dichloro-phenyl)-2-naphthalen-1-yl-pyrimidin-4-ylamine,
5-Aminomethyl-6-(2,4-dichloro-phenyl)-2-(3-methoxy-phenyl)-pyrimidin-4-ylamine,
5-Aminomethyl-6-(2,4-dichloro-phenyl)-2-(3,5-difluoro-phenyl)-pyrimidin-4-ylamine,
5-Aminomethyl-6-(2,4-dichloro-phenyl)-2-(2-methoxy-phenyl)-pyrimidin-4-ylamine,
5-Aminomethyl-6-(4-ethyl-phenyl)-2-phenyl-pyrimidin-4-ylamine,
5-Aminomethyl-6-(2,4-dichloro-phenyl)-2-isopropyl-pyrimidin-4-ylamine,
5-Aminomethyl-2-(2-chloro-4-fluoro-phenyl)-6-(2,4-dichloro-phenyl)-pyrimidin-4-ylamine,
5-Aminomethyl-2-benzo[b]thiophen-2-yl-6-(2,4-dichloro-phenyl)-pyrimidin-4-ylamine,
5-Aminomethyl-6-(2,4-dichloro-phenyl)-2-(6-methoxy-naphthalen-2-yl)-pyrimidin-4-ylamine,
5-Aminomethyl-2-phenyl-6-m-tolyl-pyrimidin-4-ylamine,
5-Aminomethyl-6-(4-chloro-phenyl)-2-phenyl-pyrimidin-4-ylamine,
5-Aminomethyl-2-phenyl-6-(4-trifluoromethyl-phenyl)-pyrimidin-4-ylamine,
5-Aminomethyl-6-(2-methoxy-phenyl)-2-phenyl-pyrimidin-4-ylamine,
5-Aminomethyl-6-(2,4-dichloro-phenyl)-2-o-tolyl-pyrimidin-4-ylamine,
5-Aminomethyl-2-(3,5-bis-trifluoromethyl-phenyl)-6-(2,4-dichloro-phenyl)-pyrimidin-4-ylamine,
5-Aminomethyl-6-(2,4-dichloro-phenyl)-2-(4-fluoro-phenoxymethyl)-pyrimidin-4-ylamine,
5-Aminomethyl-6-(2-chloro-phenyl)-2-phenyl-pyrimidin-4-ylamine,
5-Aminomethyl-6-(2-bromo-phenyl)-2-phenyl-pyrimidin-4-ylamine,
5-Aminomethyl-2-dibenzofuran-2-yl-6-(2,4-dichloro-phenyl)-pyrimidin-4-ylamine,
5-Aminomethyl-6-(2,4-bis-trifluoromethyl-phenyl)-2-phenyl-pyrimidin-4-ylamine,
5-Aminomethyl-6-(2-fluoro-4-methoxy-phenyl)-2-phenyl-pyrimidin-4-ylamine,
5-Aminomethyl-6-(2,4-dimethoxy-phenyl)-2-phenyl-pyrimidin-4-ylamine,
5-Aminomethyl-2-(1H-indol-2-yl)-6-phenyl-pyrimidin-4-ylamine,
5-Aminomethyl-6-benzo[1,3]dioxol-5-yl-2-cyclopropyl-pyrimidin-4-ylamine,
5-Aminomethyl-6-(2-fluoro-phenyl)-2-phenyl-pyrimidin-4-ylamine,
5-Aminomethyl-2-phenyl-6-(2-trifluoromethyl-phenyl)-pyrimidin-4-ylamine,
5-Aminomethyl-2-benzofuran-2-yl-6-phenyl-pyrimidin-4-ylamine,
5-Aminomethyl-6-(4-fluoro-phenyl)-2-phenyl-pyrimidin-4-ylamine,
5-Aminomethyl-2-(3,4-dimethoxy-phenyl)-6-phenyl-pyrimidin-4-ylamine,
5-Aminomethyl-6-phenyl-2-pyridin-4-yl-pyrimidin-4-ylamine,
5-Aminomethyl-6-(3-chloro-phenyl)-2-phenyl-pyrimidin-4-ylamine,
5-Aminomethyl-6-phenyl-2-thiophen-2-yl-pyrimidin-4-ylamine,
5-Aminomethyl-6-(3-fluoro-phenyl)-2-phenyl-pyrimidin-4-ylamine,
5-Aminomethyl-2,6-diphenyl-pyrimidin-4-ylamine,
5-Aminomethyl-6-(4-methoxy-phenyl)-2-phenyl-pyrimidin-4-ylamine,
5-Aminomethyl-2-phenyl-6-thiophen-3-yl-pyrimidin-4-ylamine,
5-Aminomethyl-6-(3-methoxy-phenyl)-2-phenyl-pyrimidin-4-ylamine,
6-(2,4-Dichloro-phenyl)-5-methylaminomethyl-2-phenyl-pyrimidin-4-ylamine,
3-Aminomethyl-4-(2,4-dichloro-phenyl)-6-phenyl-pyridin-2-ylamine, 3-Aminomethyl-4-(2,4-dichloro-phenyl)-5-methyl-6-phenyl-pyridin-2-ylamine,
[5-Aminomethyl-6-(4-chloro-phenyl)-2-pyridin-3-yl-pyrimidin-4-yl]-methyl-amine,
5-Aminomethyl-6-benzo[1,3]dioxol-5-yl-2-(4-methoxy-phenyl)-pyrimidin-4-ylamine,
5-Aminomethyl-6-benzo[1,3]dioxol-5-yl-2-phenyl-pyrimidin-4-ylamine,
[5-Aminomethyl-6-(4-chloro-phenyl)-2-pyridin-3-yl-pyrimidin-4-yl]-isopropyl-amine,
(5-Aminomethyl-2,6-diphenyl-pyrimidin-4-yl)-methyl-amine,
3-Aminomethyl-4-(4-chloro-phenyl)-5-methyl-6-phenyl-pyridin-2-ylamine,
3-Aminomethyl-4-(4-chloro-phenyl)-6-phenyl-pyridin-2-ylamine,
3-Aminomethyl-4,6-bis-(4-fluoro-phenyl)-pyridin-2-ylamine, and
3-Aminomethyl-4-benzo[1,3]dioxol-5-yl-6-phenyl-pyridin-2-ylamine, and pharmaceutically acceptable salts thereof.

Compounds of formula I wherein X is C—$R^5$, $R^5$ is lower alkyl and $R^3$ is ortho-substituted phenyl can exist in the form of optically pure enantiomers or as racemates. The invention embraces all of these forms.

It will be appreciated, that the compounds of formula (I) in the present invention may be derivatised at functional groups to provide derivatives which are capable of conversion back to the parent compound in vivo.

The compounds of the present invention can be prepared as outlined in Reaction Schemes I and II below:

Reaction Scheme I

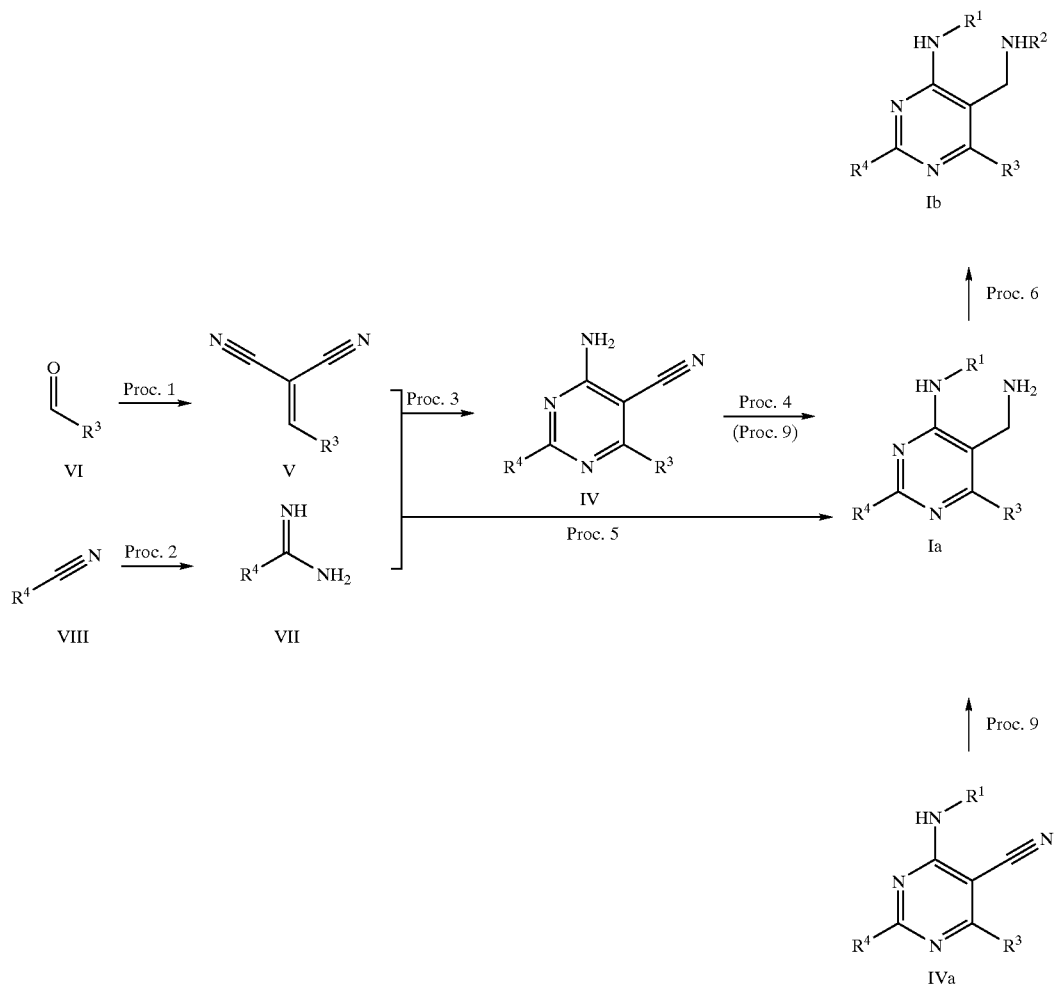

Reaction Scheme II

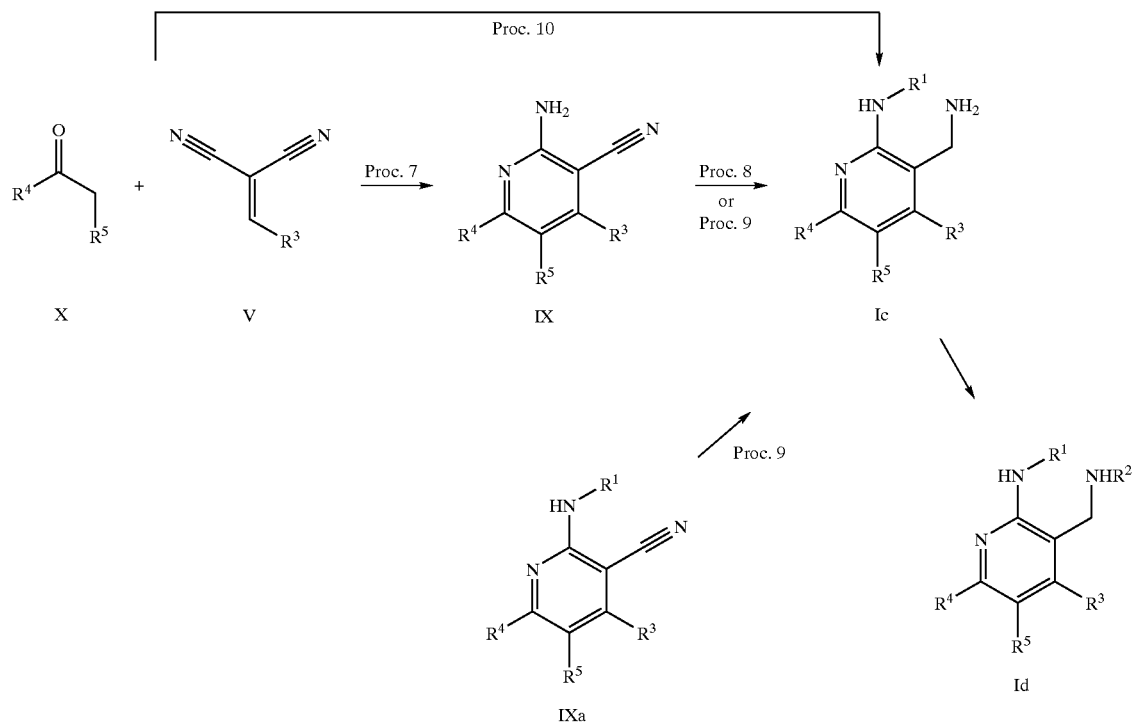

The present invention also relates to a process for the manufacture of compounds of formula I. This process comprises the reduction of nitriles of formulae IV, IVa, IX and IXa to amines of formulae Ia and Ic, respectively. This reduction can be performed according to methods known in the art. For example, the reduction can be carried out using a metal hydride such as lithium aluminum hydride in an inert solvent.

Nitriles of formulae IV and IVa are known in the art or can be prepared from arylidene malononitriles of formula V and amidines VII by processes known in the art. For example, the reaction can be performed in the presence of a base such as potassium carbonate in an inert solvent such as methanol.

Nitriles of formula IX and IXa are known in the art or can be prepared by processes known in the art. One such process is the reaction of arylidene malononitriles of formula V and ketones of formula X. For example, the reaction can be performed by heating with ammonium acetate in an inert solvent such as methanol.

Arylidene malononitriles of formula V are known in the art or can be prepared by processes known in the art, for instance by reaction of aromatic aldehydes VI with malononitrile in the presence of a base such as piperidine.

Amidines of formula VII are known in the art or can be prepared by processes known in the art. For instance, amidines of formula VII can be prepared from nitrites VIII by a process known in the art as the Pinner reaction.

Compounds of formulae Ib and Id can be prepared from corresponding compounds of formulae Ia and Ic, respectively, by an alkylation process known in the art (Bar-Haim, G.; Kol, M. Tetrahedron Lett. 1998, 39, 2663).

The compounds of formula (I) can be manufactured by the methods provided, by the methods given in the Examples or by analogous methods. Appropriate reaction conditions for the individual reaction steps are known to the person skilled in the art. Starting materials are either commercially available or can be prepared by methods analogous to the methods given below or in the Examples or by methods known in the art.

The invention further relates to compounds of formula (I) as defined above, when manufactured according to a process as defined above.

As described above, the compounds of formula (I) of the present invention can be used as medicaments for the treatment and/or prophylaxis of diseases which are associated with DPP IV such as diabetes, particularly non-insulin dependent diabetes mellitus, impaired glucose tolerance, Bowl disease, Colitis Ulcerosa, Morbus Crohn, obesity, and/or metabolic syndrome, preferably non-insulin dependent diabetes mellitus and/or impaired glucose tolerance. Furthermore, the compounds of the present invention can be used as diuretic agents or for the treatment and/or prophylaxis of hypertension.

The invention therefore also relates to pharmaceutical compositions comprising a compound as defined above and a pharmaceutically acceptable carrier. Pharmaceutically acceptable adjuvants are optionally included.

Further, the invention relates to compounds as defined above for use as therapeutic active substances, particularly as therapeutic active substances for the treatment and/or prophylaxis of diseases which are associated with DPP IV such as diabetes, particularly non-insulin dependent diabetes mellitus, impaired glucose tolerance, Bowl disease, Colitis Ulcerosa, Morbus Crohn, obesity, and/or metabolic syndrome, preferably for use as therapeutic active substances for the treatment and/or prophylaxis of non-insulin dependent diabetes mellitus and/or impaired glucose tolerance. Furthermore, the invention relates to compounds as defined above for use as diuretic agents or for use as therapeutic active substances for the treatment and/or prophylaxis of hypertension.

In another embodiment, the invention relates to a method for the treatment and/or prophylaxis of diseases which are associated with DPP IV such as diabetes, particularly non-insulin dependent diabetes mellitus, impaired glucose tolerance, Bowl disease, Colitis Ulcerosa, Morbus Crohn, obesity, and/or metabolic syndrome, preferably for the treatment and/or prophylaxis of non-insulin dependent diabetes mellitus and/or impaired glucose tolerance, which method comprises administering a compound as defined above to a human being or animal. Furthermore, the invention relates to a method for the treatment and/or prophylaxis as defined above, wherein the disease is hypertension or wherein a diuretic agent has a beneficial effect.

The invention further relates to the use of compounds as defined above for the treatment and/or prophylaxis of diseases which are associated with DPP IV such as diabetes, particularly non-insulin dependent diabetes mellitus, impaired glucose tolerance, Bowl disease, Colitis Ulcerosa, Morbus Crohn, obesity, and/or metabolic syndrome, preferably for the treatment and/or prophylaxis of non-insulin dependent diabetes mellitus and/or impaired glucose tolerance. Furthermore, the invention relates to the use as defined above, wherein the disease is hypertension or to the use as diuretic agent.

In context with the methods and uses defined above, the following diseases relate to a preferred embodiment: diabetes, particularly non-insulin dependent diabetes mellitus, impaired glucose tolerance, obesity, and/or metabolic syndrome, preferably non-insulin dependent diabetes mellitus and/or impaired glucose tolerance.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols. Depending on the nature of the active ingredient no carriers might, however, be required in the case of soft gelatine capsules. In such a case, the soft gelatine capsule would be considered a carrier, for the purposes of the present invention. Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile, the compound could be administered with one or several daily dosage units, e.g. in 1 to 3 dosage units.

The pharmaceutical preparations conveniently contain about 1–500 mg, preferably 1–100 mg, of a compound of formula I.

The following Examples serve to illustrate the present invention in more detail. They are, however, not intended to limit its scope in any manner.

EXAMPLES

Abbreviations:

MS=mass spectrometry, aq=aqueous, r.t.=room temperature, THF=tetrahydrofuran, TFA=trifluoroacetic acid, NMR=nuclear magnetic resonance spectroscopy, DMF=dimethylformamide, DMSO=dimethylsulfoxide, DCM=dichloromethane.

Example 1

Synthesis of aryl methylidene malononitriles
(Procedure 1 in Reaction Scheme I)

2-(2,4-Dichloro-benzylidene)-malononitrile

Under an atmosphere of argon, 2,4-dichlorobenzaldehyde (30.00 g, 171 mmol) and malononitrile (13.59 g, 206 mmol) were suspended in 1-butanol (350 ml). After stirring for 15 min, 8 drops of piperidine were added at room temperature. After stirring for an additional 3 h, diethyl ether was added. The precipitate was filtered and washed with diethyl ether and hexane to give the title compound, MS: m/e=222.8 (M$^+$), as a colorless solid (35.34 g, 92%).

$^1$H-NMR (300 MHz, d$^6$-DMSO, 25° C.): δ(ppm)=7.45 (1H, m), 7.59 (1H, m), 8.18 (2H, m). The following methylidene malononitriles were prepared in analogy to the procedure described above:

2-(4-Trifluoromethyl-benzylidene)-malononitrile, MS: m/e= 222.9 (M$^+$), was prepared from 4-trifluoromethyl benzaldehyde as a solid (1.35 g, 48%).

2-(2-Methyl-benzylidene)-malononitrile, MS: m/e=168.8 (M⁺), was prepared from ortho-tolyl aldehyde as a solid (1.99 g, 73%).

2-(3-Methoxy-benzylidene)-malononitrile, MS: m/e=184.7 (M⁺), was prepared from meta-anisaldehyde as a solid (1.71 g, 55%).

2-(2,4-Dimethoxy-benzylidene)-malononitrile, MS: m/e=214.8 (M⁺), was prepared from 2,4-dimethoxybenzaldehyde as a solid (2.48 g, 96%).

2-(2,4-Dimethyl-benzylidene)-malononitrile, MS: m/e=182.8 (M⁺), was prepared from 2,4-dimethylbenzaldehyde as a solid (1.75 g, 63%).

2-(2-Fluoro-4-methoxy-benzylidene)-malononitrile, MS: m/e=202.7 (M⁺), was prepared from 2-fluoro-4-methoxybenzaldehyde as a solid (1.56 g, 64%).

2-(2,4-Difluoro-benzylidene)-malononitrile, MS: m/e=190.7 (M⁺), was prepared from 2,4-difluorobenzaldehyde as a solid (2.38 g, 96%).

2-(4-Fluoro-benzylidene)-malononitrile, MS: m/e=172.8 (M⁺), was prepared from 4-fluorobenzaldehyde as a solid (1.87 g, 84%).

2-(2-Bromo-benzylidene)-malononitrile, MS: m/e=233.8 (M⁺), was prepared from 2-bromobenzaldehyde as a solid (1.59 g, 57%).

2-(2,4-Bis-trifluoromethyl-benzylidene)-malononitrile, MS: m/e=290.7 (M⁺), was prepared from 2,4-bis(trifluoromethyl)benzaldehyde as a solid (1.10 g, 92%).

2-(2-Fluoro-benzylidene)-malononitrile, MS: m/e=172.9 (M⁺), was prepared from 2-fluorobenzaldehyde as a solid (1.55 g, 75%).

2-Thiophen-3-ylmethylene-malononitrile was prepared from 3-thiophenecarbaldehyde as a solid (0.4 g, 21%).

2-(3-Fluoro-benzylidene)-malononitrile, MS: m/e=160.8 (M⁺), was prepared from 3-fluorobenzaldehyde as a solid (1.72 g, 83%).

2-(3-Methyl-benzylidene)-malononitrile, MS: m/e=168.7 (M⁺), was prepared from m-tolylaldehyde as a solid (0.74 g, 37%).

2-(2-Trifluoromethyl-benzylidene)-malononitrile, MS: m/e=222.8 (M⁺), was prepared from 2-trifluoromethylbenzaldehyde as a solid (2.20 g, 83%).

2-Benzo[1,3]dioxol-5-ylmethylene-malononitrile, MS: m/e=189.8 (M⁺), was prepared from piperonal as a solid (19.4 g, 98%).

2-(4-Methyl-benzylidene)-malononitrile, MS: m/e=168.9 (M⁺), was prepared from 4-methylbenzaldehyde as a solid.

2-(4-Chloro-benzylidene)-malononitrile, MS: m/e=188.7 (M⁺), was prepared from 4-chlorobenzaldehyde as a solid.

2-(2-Methoxy-benzylidene)-malononitrile, MS: m/e=184.8 (M⁺), was prepared from 2-methoxybenzaldehyde as a solid.

2-(2-Chloro-benzylidene)-malononitrile, MS: m/e=188.9 (M⁺), was prepared from 2-chlorobenzaldehyde as a solid.

2-(3-Chloro-benzylidene)-malononitrile, MS: m/e=188.9 (M⁺), was prepared from 3-chlorobenzaldehyde as a solid.

2-(4-Methoxy-benzylidene)-malononitrile, MS: m/e=184.7 (M⁺), was prepared from 4-methoxybenzaldehyde as a solid.

2-Thiophen-3-ylmethylene-malononitrile, MS: m/e=160.8 (M⁺), was prepared from 3-thiophenecarbaldehyde as a solid.

2-(3-Methoxy-benzylidene)-malononitrile, MS: m/e=184.8 (M⁺), was prepared from 3-methoxybenzaldehyde as a solid.

Example 2

Synthesis of Benzamidines (Procedure 2 in Reaction Scheme I)

3,5-Dimethoxy-benzamidine

Dry HCl gas was bubbled through a cooled (−15° C.) solution of 3,5-dimethoxybenzonitrile (1.50 g, 9.20 mmol) for 30 minutes. The reaction mixture was placed in a refrigerator overnight. After evaporation of the solvent, a white solid was obtained which was dissolved in ethanol. 9.2 ml of a 2molar solution of ammonia in Methanol was added and the reaction mixture was stirred at room temperature overnight. After evaporation of the solvent, the title compound, MS: m/e=181.2 (M+H⁺), (1.21 g, 71%) was obtained by chromatographic purification of the residue (silica gel, MeOH, DCM).

$^1$H-NMR (300 MHz, d$^6$-DMSO, 25° C.):δ(ppm)=3.80 (6H, s), 6.82 (1H, t, J=2 Hz), 7.05 (2H, t, J=2 Hz), 9.35 (3H, bs).

The following benzamidines were prepared in analogy to the procedure described above:

3-Trifluoromethyl-benzamidine, MS: m/e=189.2 (M+H⁺), was prepared from 3-trifluoromethyl-benzonitrile as a solid (1.14 g, 69%).

2-Methoxy-benzamidine, MS: m/e=151.2 (M+H⁺), was prepared from 2-methoxybenzonitrile as a solid (113 mg, 7%).

3,4,5-Trimethoxy-benzamidine, MS: m/e=211.3 (M+H⁺), was prepared from 3,4,5-trimethoxy-benzaldehyde as a solid.

3,4-Dimethoxy-benzamidine, MS: m/e=181.2 (M+H⁺), was prepared from 3,4-dimethoxy-benzaldehyde as a solid.

Thiophene-2-carboxamidine, MS: m/e=127.1 (M+H⁺), was prepared from thiophene-3-carbonitrile as a solid.

2-Fluorobenzamidine, MS: m/e=139.2 (M+H⁺), was prepared from 2-fluorobenzonitrile as a solid.

4-Chlorobenzamidine, MS: m/e=154.2 (M+H⁺), was prepared from 4-chlorobenzonitrile as a solid.

4-Methylbenzamidine, MS: m/e=135.1 (M+H⁺), was prepared from 4-methylbenzonitrile as a solid.

4-Methoxybenzamidine, MS: m/e=151.3 (M+H⁺), was prepared from 4-methoxybenzonitrile as a solid.

Benzo[1,3]dioxole-5-carboxamidine, MS: m/e=165.2 (M+H⁺), was prepared from benzo[1,3]dioxole-5-carbonitrile as a solid.

Naphthalene-1-carboxamidine, MS: m/e=171.2 (M+H⁺), was prepared from naphthalene-1-carbonitrile as a solid.

3-Methoxy-benzamidine, MS: m/e=151.3 (M+H⁺), was prepared from 3-methoxy-benzonitrile as a solid.

2-Chloro-4-fluorobenzamidine, MS: m/e=173.1 (M+H⁺), was prepared from 3-chloro-4-fluorobenzonitrile as a solid.

2-Methylbenzamidine, MS: m/e=134.1 (M+H⁺), was prepared from 2-methyl-benzonitrile as a solid.

1H-indole-2-carboxamidine, MS: m/e=160.2 (M+H⁺), was prepared from 1H-indole-2-carbonitrile as a solid.

Benzofuran-2-carboxamidine, MS: m/e=161.3 (M+H⁺), was prepared from benzofuran-2-carbonitrile as a solid.

Isonicotinamidine, MS: m/e=122.2 (M+H⁺), was prepared from 4-cyanopyridine as a solid.

Example 3

Synthesis of 4-Amino-pyrimidine-5-carbonitriles
(Procedure 3 in Reaction Scheme I)

4-Amino-6-(2,4-dichloro-phenyl)-2-phenyl-pyrimidine-5-carbonitrile

Potassium carbonate (4.34 g, 31.4 mmol) and benzamidine (2.59 g, 21.5 mmol) were added at to a suspension of 2-(2,4-dichloro-benzylidene)-malononitrile (4 g, 17.9 mmol) in methanol. The yellow mixture was stirred for 1 h at room temperature and then heated to reflux for an additional 2 h. After cooling, the solvent was removed at reduced pressure, the residue was taken up in ethyl acetate/ice. The organic phase was separated, washed with water, and dried over sodium sulfate. The solvent was evaporated, the orange residue was taken up in acetone, and 1.91 g potassium manganate was added. After stirring for 90 min, the reaction mixture was filtered through decalite and evaporated. Purification by flash chromatography (silica gel, EtOAc/hexanes) afforded the title compound, MS: m/e=340.8 (M$^+$), as a solid (2.63 g, 43%).

$^1$H-NMR (300 MHz, d$^6$-DMSO, 25° C.): δ(ppm)= 7.48–7.60 (3H, m), 7.62–7.68 (2H, m), 7.77 (1H, s), 8.30 (2H, bs), 8.60–8.70 (2H, m).

The following 4-Amino-pyrimidine-5-carbonitriles were prepared in analogy to the procedure described above:

4-Amino-6-benzo[1,3]dioxol-5-yl-2-phenyl-pyrimidine-5-carbonitrile, MS: m/e=315.9 (M$^+$), was prepared from 2-benzo[1,3]dioxol-5-ylmethylene-malononitrile as a solid (629 mg, 23%).

4-Amino-6-benzo[1,3]dioxol-5-yl-2-(4-methoxy-phenyl)-pyrimidine-5-carbonitrile, MS: m/e=346.2 (M$^+$), was prepared from 2-benzo[1,3]dioxol-5-ylmethylene-malononitrile and p-Methoxybenzamidine as a solid (78 mg, 26%).

4-Amino-2-phenyl-6-(4-trifluoromethyl-phenyl)-pyrimidine-5-carbonitrile, MS: m/e=340.1 (M$^+$), was prepared from 2-(4-trifluoromethyl-benzylidene)-malononitrile as a solid (312 mg, 20%).

4-Amino-2-phenyl-6-o-tolyl-pyrimidine-5-carbonitrile, MS: m/e=286.8 (M+H$^+$), was prepared from 2-(2-methyl-benzylidene)-malononitrile as a solid (700 mg, 22%).

4-Amino-6-(3-methoxy-phenyl)-2-phenyl-pyrimidine-5-carbonitrile, MS: m/e=301.8(M$^+$), was prepared from 2-(3-methoxy-benzylidene)-malononitrile as a solid (391 mg, 15%).

4-Amino-2-phenyl-6-m-tolyl-pyrimidine-5-carbonitrile, MS: m/e=286.1 (M$^+$), was prepared from 2-(3-methyl-benzylidene)-malononitrile as a solid (515 mg, 28%).

4-Amino-2-phenyl-6-p-tolyl-pyrimidine-5-carbonitrile, MS: m/e=286.0 (M$^+$), was prepared from 2-(4-methyl-benzylidene)-malononitrile as a solid (3.13 g, 37%).

4-Amino-6-(2,4-dichloro-phenyl)-2-(3-methoxy-phenyl)-pyrimidine-5-carbonitrile, MS: m/e=371.2 (M+H$^+$), was prepared from 2-(2,4-dichloro-benzylidene)-malononitrile and 3-methoxybenzamidine as a solid (17 mg, 32%).

4-Amino-6-(2,4-difluoro-phenyl)-2-phenyl-pyrimidine-5-carbonitrile was prepared from 2-(2,4-difluoro-benzylidene)-malononitrile as a solid (430 mg, 88%).

4-Amino-6-(2,4-dichloro-phenyl)-2-m-tolyl-pyrimidine-5-carbonitrile, MS: m/e=308.1 (M$^+$), was prepared from 2-(2,4-dichloro-benzylidene)-malononitrile and 3-methylbenzamidine as a solid (150 mg, 87%).

4-Amino-6-(2,4-dichloro-phenyl)-2-(3,4,5-trimethoxy-phenyl)-pyrimidine-5-carbonitrile, MS: m/e=430.0 (M$^+$), was prepared from 2-(2,4-dichloro-benzylidene)-malononitrile and 3,4,5-trimethoxy-benzamidine as a solid (1.4 g, 96%).

Example 4

Synthesis of 5-Aminomethyl-pyrimidin-4-ylamines
(Procedure 4 in Reaction Scheme I)

5-Aminomethyl-6-(2,4-dichloro-phenyl)-2-phenyl-pyrimidin-4-ylamine

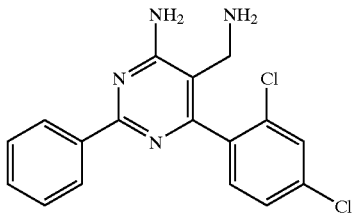

Under an atmosphere of argon, a solution of 4-Amino-6-(2,4-dichloro-phenyl)-2-phenyl-pyrimidine-5-carbonitrile (1.16 g, 0.34 mmol) in THF (6 ml) was added slowly to a suspension of LiAlH$_4$ in THF (3 ml). After stirring for 2 h at 40° C., the reaction mixture was cooled to −20° C. and water (0.6 ml) was added. After 15 min, ethyl acetate was added and the mixture was filtered through Decalite. The organic phase was then separated, washed with water, and dried over sodium sulfate. Purification by flash chromatography (silica gel, methanol, dichloromethane) afforded the title compound, MS: m/e=344.2 (M$^+$), as a light yellow solid (0.446 g, 40%).

$^1$H-NMR (300 MHz, d$^6$-DMSO, 25° C.): δ(ppm)=3.35 (1H, d, J=11 Hz), 3.50 (1H, d, J=11 Hz), 7.28 (bs, 2H), 7.38–7.46 (3H, m), 7.50–7.58 (2H, m), 7.75 (1H, m), 8.20–8.30 (2H, m).

Example 5

5-Aminomethyl-2-phenyl-6-p-tolyl-pyrimidin-4-ylamine

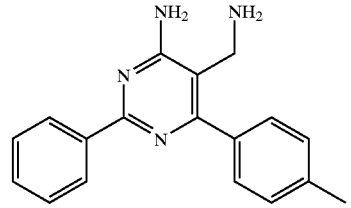

The title compound, MS: m/e=289.9 (M$^+$), was prepared from 4-amino-2-phenyl-6-p-tolyl-pyrimidine-5-carbonitrile in analogy to the process described in Example 4 as a solid (190 mg, 37%).

Example 6

5-Aminomethyl-6-(2,4-dichloro-phenyl)-2-(3-methoxy-phenyl)-pyrimidin-4-ylamine

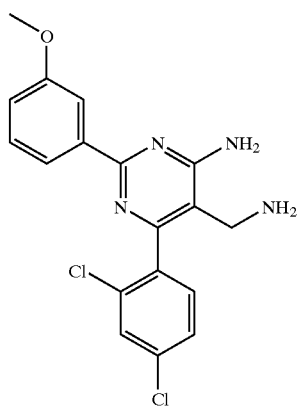

The title compound, MS: m/e=374.9 (M+), was prepared from 4-amino-6-(2,4-dichloro-phenyl)-2-(3-methoxy-phenyl)-pyrimidine-5-carbonitrile in analogy to the process described in Example 4 as a solid (1.5 mg, 9%).

Example 7

5-Aminomethyl-2-phenyl-6-o-tolyl-pyrimidin-4-ylamine

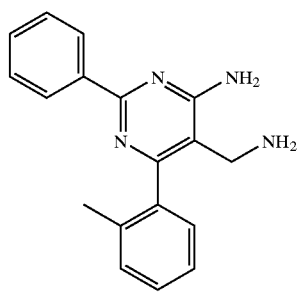

The title compound, MS: m/e=290.8 (M+H+), was prepared from 4-amino-2-phenyl-6-o-tolyl-pyrimidine-5-carbonitrile in analogy to the process described in Example 4 as a solid (62 mg, 31%).

Example 8

5-Aminomethyl-6-(2,4-difluoro-phenyl)-2-phenyl-pyrimidin-4-ylamine

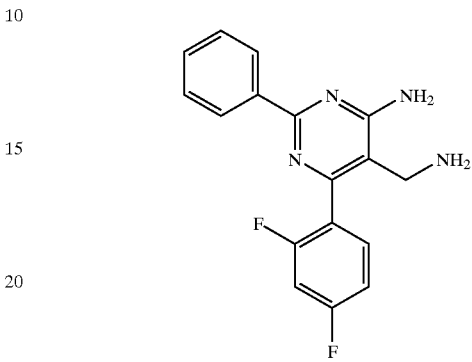

The title compound, MS: m/e=312.1 (M+), was prepared from 4-amino-2-phenyl-6-o-tolyl-pyrimidine-5-carbonitrile in analogy to the process described in Example 4 as a solid (21 mg, 10%).

Example 9

5-Aminomethyl-6-(2,4-dichloro-phenyl)-2-m-tolyl-pyrimidin-4-ylamine

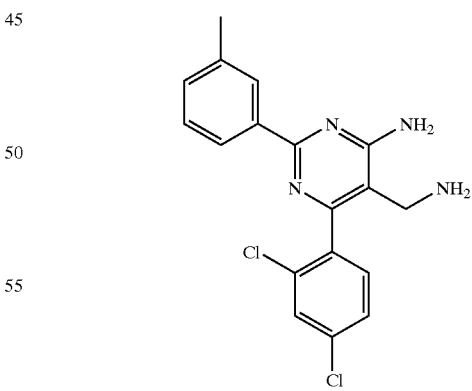

The title compound, MS: m/e=359.1 (M+H+), was prepared from 4-amino-6-(2,4-dichloro-phenyl)-2-m-tolyl-pyrimidine-5-carbonitrile in analogy to the process described in Example 4 as a solid (1.4 mg, 92%).

Example 10

5-Aminomethyl-6-(2,4-dichloro-phenyl)-2-(3,4,5-trimethoxy-phenyl)-pyrimidin-4-ylamine

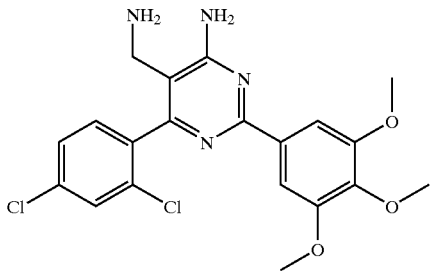

The title compound, MS: m/e=434.9 (M$^+$), was prepared from 4-amino-6-(2,4-dichloro-phenyl)-2-(3,4,5-trimethoxy-phenyl)-pyrimidine-5-carbonitrile in analogy to the process described in Example 4 as a solid (164 mg, 12%).

Example 11

5-Aminomethyl-pyrimidin-4-ylamines by High-Throughput Synthesis from aryl methylidene malononitriles (Procedure 5 in Reaction Scheme I)

5-Aminomethyl-6-(2,4-dimethyl-phenyl)-2-phenyl-pyrimidin-4-ylamine

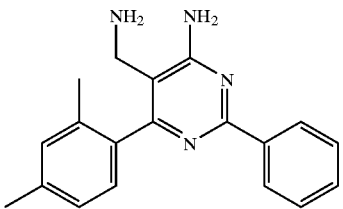

Benzamidine (48 mg, 0.4 mmol) and potassium carbonate (97 mg, 0.7 mmol) were placed in a reaction vial and suspended in 2 ml MeOH. 2-(2,4-dimethyl-benzylidene)-malononitrile (87 mg, 0.48 mmol) was added, the vial was stoppered and shaken first for 30 min at r.t., then for 3 h at 60° C. After cooling, the mixture was filtered and the filtrate was evaporated in a vacuum zentrifuge (45° C.). The residue was dissolved in 2 ml of acetone, 63 mg (0.4 mmol) KMnO$_4$ was added, and the mixture was shaken for 2 h at rt. The reaction mixture was then filtered and the filtrate evaporated in a vacuum zentrifuge (45° C.). Purification of the re-dissolved (DMF, 1 ml) residue by automated, preparative HPLC (YMC CombiPrep C18 column 50×20 mm, solvent gradient 5–95% CH$_3$CN in 0.1% TFA(aq) over 6.0 min, λ=230 nm, flow rate 40 ml/min) gave 22 mg of an intermediate which was dissolved in THF (1 ml) and added, under an atmosphere of argon, to a cooled (0° C.) suspension of 100 mg of Lithium aluminium hydride in 1 ml THF in a reaction vial. The reaction mixture was shaken first for 2 h at r.t. and subsequently for 4 h at 40° C. Upon cooling, water was added carefully and the mixture was filtered. The filtrate was evaporated in a vacuum zentrifuge (45° C.). Purification of the re-dissolved (DMF, 1 ml) residue by automated, preparative HPLC (YMC CombiPrep C18 column 50×20 mm, solvent gradient 5–95% CH$_3$CN in 0.1% TFA(aq) over 6.0 min, λ=230 nm, flow rate 40 ml/min) gave 8 mg (7%) of the title compound, MS: m/e=304.9 (M$^+$), as a solid.

Example 12

5-Aminomethyl-6-(2,4-dichloro-phenyl)-2-(3,5-dimethoxy-phenyl)-pyrimidin-4-ylamine

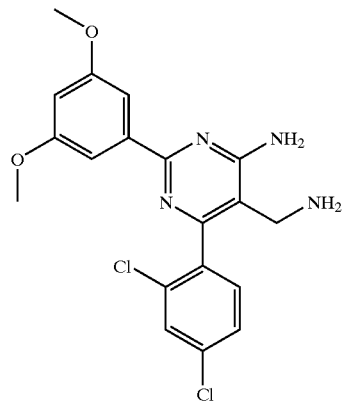

The title compound, MS: m/e=405.4 (M+H$^+$), was prepared from 3,5-dimethoxy-benzamidine and 2-(2,4-dichloro-benzylidene)-malononitrile in analogy to the process described in Example 11 as a solid.

Example 13

5-Aminomethyl-6-(2,4-dichloro-phenyl)-2-(3-fluoro-phenyl)-pyrimidin-4-ylamine

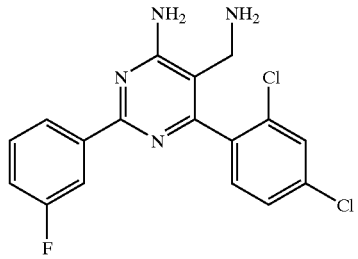

The title compound, MS: m/e=362.9 (M+H$^+$), was prepared from 3-fluoro-benzamidine and 2-(2,4-dichloro-benzylidene)-malononitrile in analogy to the process described in Example 11 as a solid.

Example 14

5-Aminomethyl-6-(2,4-dichloro-phenyl)-2-(4-fluoro-phenyl)-pyrimidin-4-ylamine

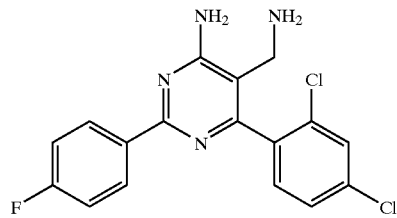

The title compound, MS: m/e=362.9 (M+H$^+$), was prepared from 4-fluoro-benzamidine and 2-(2,4-dichloro-benzylidene)-malononitrile in analogy to the process described in Example 11 as a solid.

Example 15

5-Aminomethyl-6-(2,4-dichloro-phenyl)-2-(4-methoxy-1-methyl-1H-indol-6-yl)-pyrimidin-4-ylamine

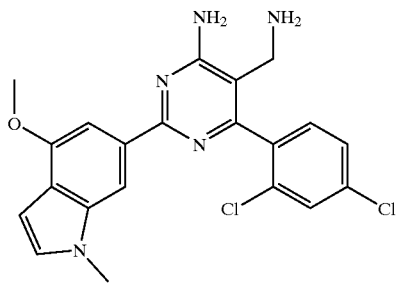

The title compound, MS: m/e=428.0 (M+H⁺), was prepared from 4-methoxy-1-methyl-1H-indole-6-carboxamidine and 2-(2,4-dichloro-benzylidene)-malononitrile in analogy to the process described in Example 11 as a solid.

Example 16

5-Aminomethyl-2-benzofuran-2-yl-6-(2,4-dichloro-phenyl)-pyrimidin-4-ylamine

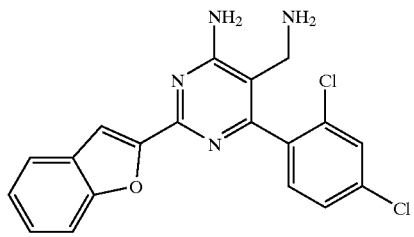

The title compound, MS: m/e=385.3 (M+H⁺), was prepared from benzofuran-2-carboxamidine and 2-(2,4-dichloro-benzylidene)-malononitrile in analogy to the process described in Example 11 as a solid.

Example 17

5-Aminomethyl-6-(2,4-dichloro-phenyl)-2-(1H-indol-2-yl)-pyrimidin-4-ylamine

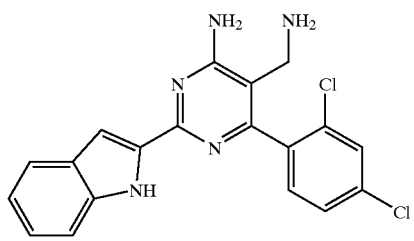

The title compound, MS: m/e=383.9 (M+H⁺), was prepared from 1H-indole-2-carboxamidine and 2-(2,4-dichloro-benzylidene)-malononitrile in analogy to the process described in Example 11 as a solid.

Example 18

5-Aminomethyl-6-(2,4-dichloro-phenyl)-2-m-tolyl-pyrimidin-4-ylamine

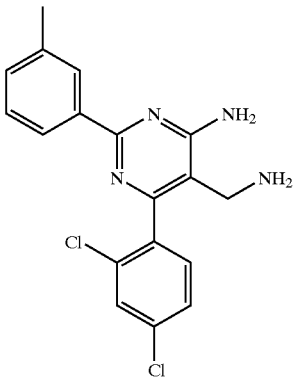

The title compound, MS: m/e=359.1 (M+H⁺), was prepared from 3-methyl-benzamidine and 2-(2,4-dichloro-benzylidene)-malononitrile in analogy to the process described in Example 11 as a solid.

Example 19

2-(4-Amino-3-methoxy-phenyl)-5-aminomethyl-6-(2,4-dichloro-phenyl)-pyrimidin-4-ylamine

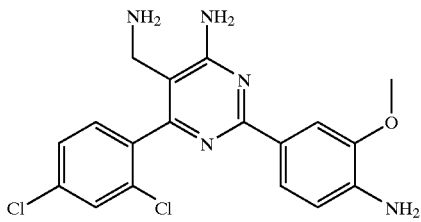

The title compound, MS: m/e=389.9 (M+H⁺), was prepared from 4-amino-3-methoxy-benzamidine and 2-(2,4-dichloro-benzylidene)-malononitrile in analogy to the process described in Example 11 as a solid.

Example 20

5-Aminomethyl-2-azepan-1-yl-6-(2,4-dichloro-phenyl)-pyrimidin-4-ylamine

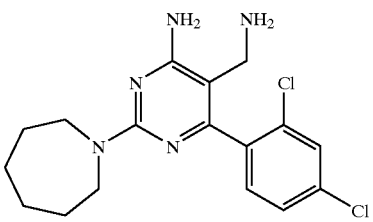

The title compound, MS: m/e=366.0 (M+H⁺), was prepared from azepane-1-carboxamidine and 2-(2,4-dichloro-benzylidene)-malononitrile in analogy to the process described in Example 11 as a solid.

Example 21

5-Aminomethyl-6-(2,4-dichloro-phenyl)-2-(3,4-difluoro-phenyl)-pyrimidin-4-ylamine

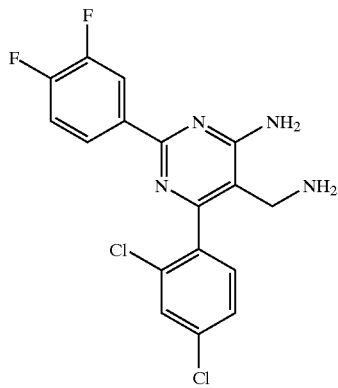

The title compound, MS: m/e=381.3 (M+H$^+$), was prepared from 3,4-difluoro-benzamidine and 2-(2,4-dichloro-benzylidene)-malononitrile in analogy to the process described in Example 11 as a solid.

Example 22

5-Aminomethyl-6-(2,4-dichloro-phenyl)-2-pyrrolidin-1-yl-pyrimidin-4-ylamine

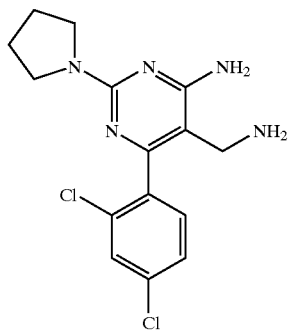

The title compound, MS: m/e=337.8 (M$^+$), was prepared from pyrrolidine-1-carboxamidine and 2-(2,4-dichloro-benzylidene)-malononitrile in analogy to the process described in Example 11 as a solid.

Example 23

5-Aminomethyl-6-(2,4-dichloro-phenyl)-2-methylsulfanyl-pyrimidin-4-ylamine

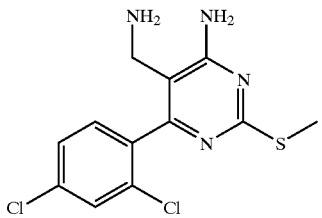

The title compound, MS: m/e=315.2 (M$^+$), was prepared from 2-methyl-isothiourea and 2-(2,4-dichloro-benzylidene)-malononitrile in analogy to the process described in Example 11 as a solid.

Example 24

5-Aminomethyl-6-(2,4-dichloro-phenyl)-2-(3,4-dimethoxy-phenyl)-pyrimidin-4-ylamine

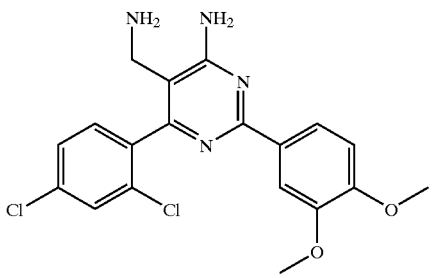

The title compound, MS: m/e=405.3 (M+H$^+$), was prepared from 3,4-dimethoxy-benzamidine and 2-(2,4-dichloro-benzylidene)-malononitrile in analogy to the process described in Example 11 as a solid.

Example 25

5-Aminomethyl-6-(2,4-dichloro-phenyl)-2-thiophen-2-yl-pyrimidin-4-ylamine

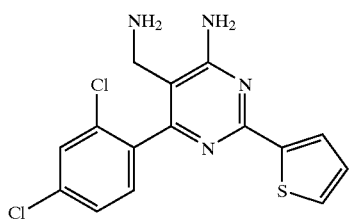

The title compound, MS: m/e=351.2 (M+H$^+$), was prepared from thiophene-2-carboxamidine and 2-(2,4-dichloro-benzylidene)-malononitrile in analogy to the process described in Example 11 as a solid.

Example 26

5-Aminomethyl-6-(2,4-dichloro-phenyl)-2-(2-fluoro-phenyl)-pyrimidin-4-ylamine

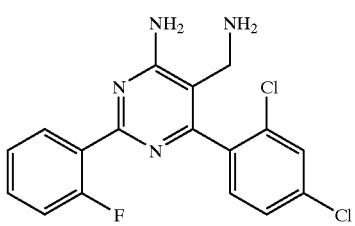

The title compound, MS: m/e=363.0 (M+H$^+$), was prepared from 2-fluorobenzamidine and 2-(2,4-dichloro-benzylidene)-malononitrile in analogy to the process described in Example 11 as a solid.

Example 27

5-Aminomethyl-2-(4-chloro-phenyl)-6-(2,4-dichloro-phenyl)-pyrimidin-4-ylamine

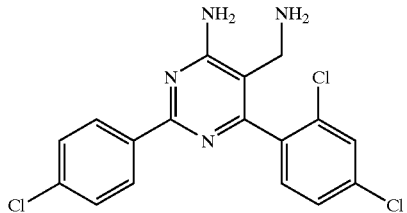

The title compound, MS: m/e=377.8 (M⁺), was prepared from 4-chloro-benzamidine and 2-(2,4-dichloro-benzylidene)-malononitrile in analogy to the process described in Example 11 as a solid.

Example 28

5-Aminomethyl-6-(2,4-dichloro-phenyl)-2-methoxy-pyrimidin-4-ylamine

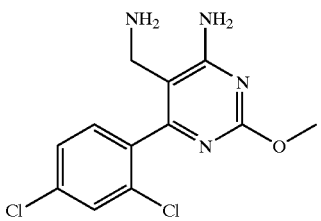

The title compound, MS: m/e=337.8 (M⁺), was prepared from 2-methyl-isourea and 2-(2,4-dichloro-benzylidene)-malononitrile in analogy to the process described in Example 11 a solid.

Example 29

5-Aminomethyl-2-cyclopropyl-6-phenyl-pyrimidin-4-ylamine

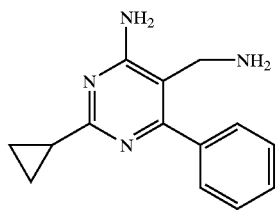

The title compound, MS: m/e=240.1 (M⁺), was prepared from cyclopropanecarboxamidine and 2-benzylidene-malononitrile in analogy to the process described in Example 11 as a solid.

Example 30

5-Aminomethyl-6-(2,4-dichloro-phenyl)-2-p-tolyl-pyrimidin-4-ylamine

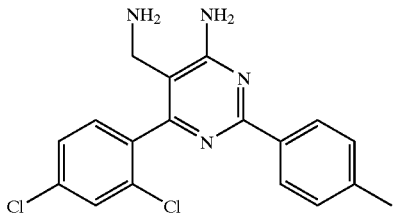

The title compound, MS: m/e=358.2 (M⁺), was prepared from 4-methylbenzamidine and 2-(2,4-dichloro-benzylidene)-malononitrile in analogy to the process described in Example 11 as a solid.

Example 31

5-Aminomethyl-6-(2,4-dichloro-phenyl)-2-(4-methoxy-phenyl)-pyrimidin-4-ylamine

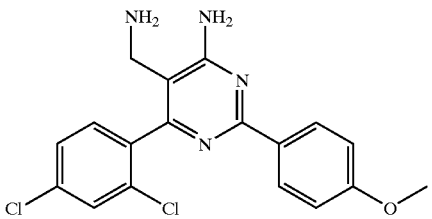

The title compound, MS: m/e=375.3 (M+H⁺), was prepared from 4-methoxybenzamidine and 2-(2,4-dichloro-benzylidene)-malononitrile in analogy to the process described in Example 11 as a solid.

Example 32

5-Aminomethyl-2-benzo[1,3]dioxol-5-yl-6-(2,4-dichloro-phenyl)-pyrimidin-4-ylamine

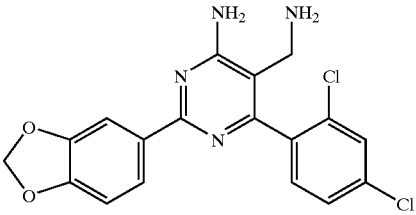

The title compound, MS: m/e=388.2 (M⁺), was prepared from benzo[1,3]dioxole-5-carboxamidine and 2-(2,4-dichloro-benzylidene)-malononitrile in analogy to the process described in Example 11 as a solid.

Example 33

5-Aminomethyl-6-(2,4-dichloro-phenyl)-2-(3-trifluoromethyl-phenyl)-pyrimidin-4-ylamine

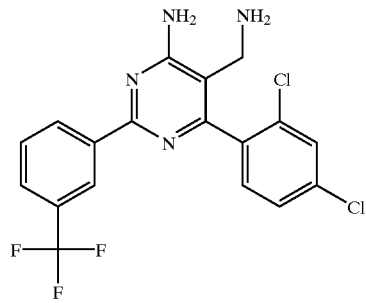

The title compound, MS: m/e=412.9 (M+H$^+$), was prepared from 3-trifluoromethyl-benzamidine and 2-(2,4-dichloro-benzylidene)-malononitrile in analogy to the process described in Example 11 as a solid.

Example 34

5-Aminomethyl-6-(2,4-dichloro-phenyl)-2-morpholin-4-yl-pyrimidin-4-ylamine

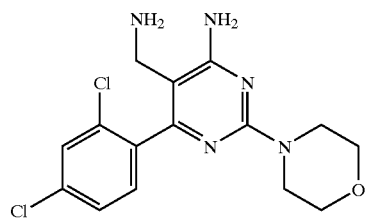

The title compound, MS: m/e=353.9 (M$^+$), was prepared from morpholine-4-carboxamidine and 2-(2,4-dichloro-benzylidene)-malononitrile in analogy to the process described in Example 11 as a solid.

Example 35

5-Aminomethyl-6-(2,4-dichloro-phenyl)-2-(4-trifluoromethyl-phenyl)-pyrimidin-4-ylamine

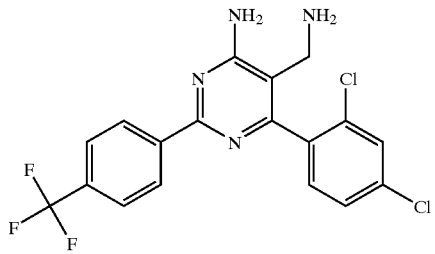

The title compound, MS: m/e=412.9 (M+H$^+$), was prepared from 4-trifluoromethyl-benzamidine and 2-(2,4-dichloro-benzylidene)-malononitrile in analogy to the process described in Example 11 as a solid.

Example 36

5-Aminomethyl-2-(3-chloro-phenyl)-6-(2,4-dichloro-phenyl)-pyrimidin-4-ylamine

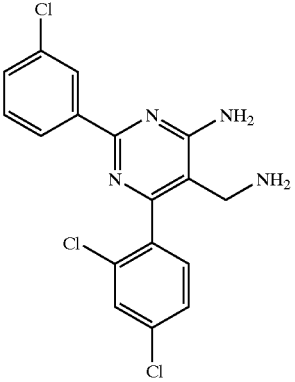

The title compound, MS: m/e=378.8 (M+H$^+$), was prepared from 3-chlorobenzamidine and 2-(2,4-dichloro-benzylidene)-malononitrile in analogy to the process described in Example 11 as a solid.

Example 37

5-Aminomethyl-6-(2,4-dichloro-phenyl)-2-methyl-pyrimidin-4-ylamine

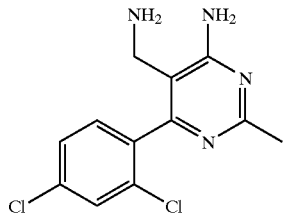

The title compound, MS: m/e=282.9 (M+H$^+$), was prepared from acetamidine and 2-(2,4-dichloro-benzylidene)-malononitrile in analogy to the process described in Example 11 as a solid.

Example 38

5-Aminomethyl-6-(2,4-dichloro-phenyl)-2-naphthalen-2-yl-pyrimidin-4-ylamine

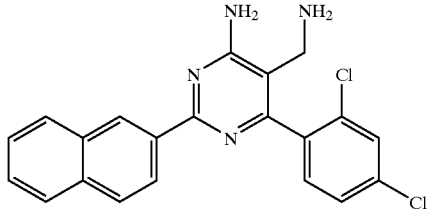

The title compound, MS: m/e=394.9 (M+H$^+$), was prepared from naphthalene-2-carboxamidine and 2-(2,4-dichloro-benzylidene)-malononitrile in analogy to the process described in Example 11 as a solid.

Example 39

5-Aminomethyl-6-(2,4-dichloro-phenyl)-2-naphthalen-1-yl-pyrimidin-4-ylamine

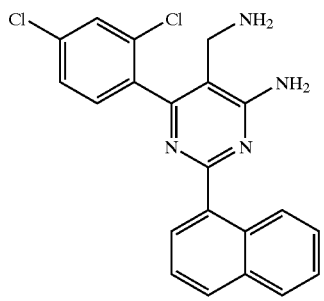

The title compound, MS: m/e=395.3 (M+H$^+$), was prepared from naphthalene-1-carboxamidine and 2-(2,4-dichloro-benzylidene)-malononitrile in analogy to the process described in Example 11 as a solid.

Example 40

5-Aminomethyl-6-(2,4-dichloro-phenyl)-2-(3-methoxy-phenyl)-pyrimidin-4-ylamine

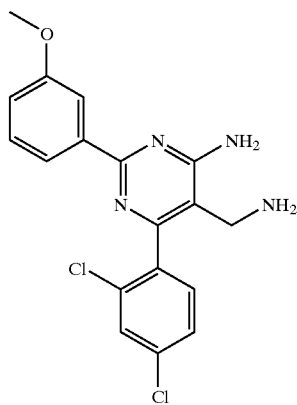

The title compound, MS: m/e=374.8 (M$^+$), was prepared from 3-methoxybenzamidine and 2-(2,4-dichloro-benzylidene)-malononitrile in analogy to the process described in Example 11 as a solid.

Example 41

5-Aminomethyl-6-(2,4-dichloro-phenyl)-2-(3,5-difluoro-phenyl)-pyrimidin-4-ylamine

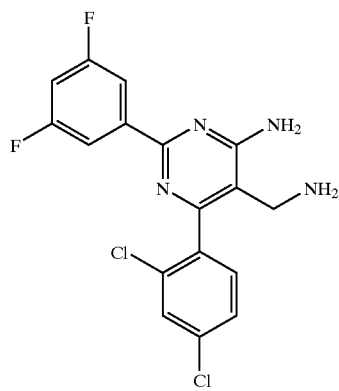

The title compound, MS: m/e=380.9 (M+H$^+$), was prepared from 3,5-difluorobenzamidine and 2-(2,4-dichloro-benzylidene)-malononitrile in analogy to the process described in Example 11 as a solid.

Example 42

5-Aminomethyl-6-(2,4-dichloro-phenyl)-2-(2-methoxy-phenyl)-pyrimidin-4-ylamine

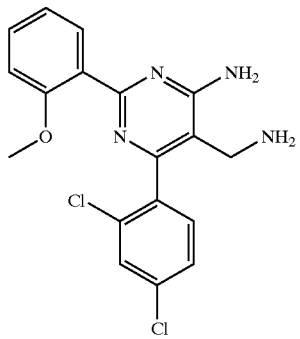

The title compound, MS: m/e=374.8 (M+H$^+$), was prepared from 2-methoxybenzamidine and 2-(2,4-dichloro-benzylidene)-malononitrile in analogy to the process described in Example 11 as a solid.

Example 43

5-Aminomethyl-6-(4-ethyl-phenyl)-2-phenyl-pyrimidin-4-ylamine

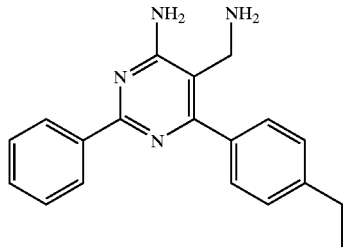

The title compound, MS: m/e=304.8 (M+H⁺), was prepared from 2-(4-ethyl-benzylidene)-malononitrile in analogy to the process described in Example 11 as a solid.

Example 44

5-Aminomethyl-6-(2,4-dichloro-phenyl)-2-isopropyl-pyrimidin-4-ylamine

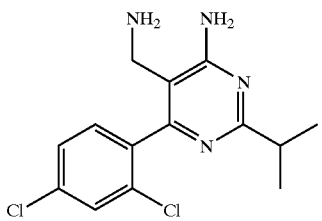

The title compound, MS: m/e=311.2 (M+H⁺), was prepared from isobutyramidine and 2-(2,4-dichloro-benzylidene)-malononitrile in analogy to the process described in Example 11 as a solid.

Example 45

5-Aminomethyl-2-(2-chloro-4-fluoro-phenyl)-6-(2,4-dichloro-phenyl)-pyrimidin-4-ylamine

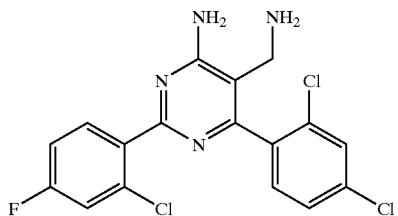

The title compound, MS: m/e=396.8 (M⁺), was prepared from 2-chlor-4-fluoro-benzamidine and 2-(2,4-dichloro-benzylidene)-malononitrile in analogy to the process described in Example 11 as a solid.

Example 46

5-Aminomethyl-2-benzo[b]thiophen-2-yl-6-(2,4-dichloro-phenyl)-pyrimidin-4-ylamine

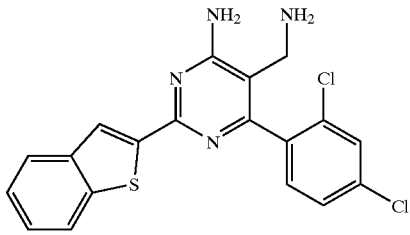

The title compound, MS: m/e=400.9 (M+H⁺), was prepared from benzo[b]thiophene-2-carboxamidine and 2-(2,4-dichloro-benzylidene)-malononitrile in analogy to the process described in Example 11 as a solid.

Example 47

5-Aminomethyl-6-(2,4-dichloro-phenyl)-2-(6-methoxy-naphthalen-2-yl)-pyrimidin-4-ylamine

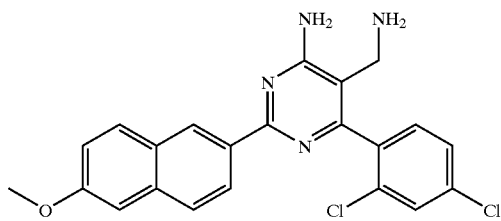

The title compound, MS: m/e=425.0 (M+H⁺), was prepared from 6-methoxy-naphthalene-2-carboxamidine and 2-(2,4-dichloro-benzylidene)-malononitrile in analogy to the process described in Example 11 as a solid.

Example 48

5-Aminomethyl-2-phenyl-6-m-tolyl-pyrimidin-4-ylamine

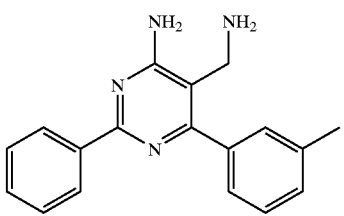

The title compound, MS: m/e=291.2 (M+H⁺), was prepared from 4-Amino-2-phenyl-6-m-tolyl-pyrimidine-5-carbonitrile in analogy to the process described in Example 11 as a solid.

Example 49

5-Aminomethyl-6-(4-chloro-phenyl)-2-phenyl-pyrimidin-4-ylamine

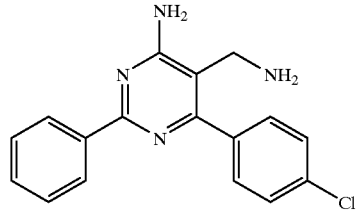

The title compound MS: m/e=311.0 (M+H$^+$), was prepared from 2-(4-chloro-benzylidene)-malononitrile in analogy to the process described in Example 11 as a solid.

Example 50

5-Aminomethyl-2-phenyl-6-(4-trifluoromethyl-phenyl)-pyrimidin-4-ylamine

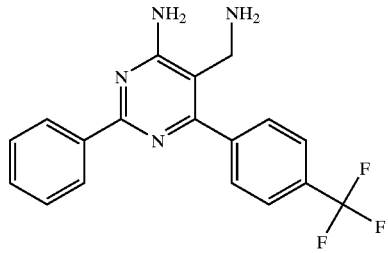

The title compound, MS: m/e=344.0 (M$^+$), was prepared from 2-(4-trifluoromethyl-benzylidene)-malononitrile in analogy to the process described in Example 11 as a solid.

Example 51

5-Aminomethyl-6-(2-methoxy-phenyl)-2-phenyl-pyrimidin-4-ylamine

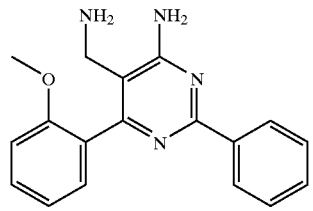

The title compound, MS: m/e=306.8 (M$^+$), was prepared from 2-(2-methoxy-benzylidene)-malononitrile in analogy to the process described in Example 11 as a solid.

Example 52

5-Aminomethyl-6-(2,4-dichloro-phenyl)-2-o-tolyl-pyrimidin-4-ylamine

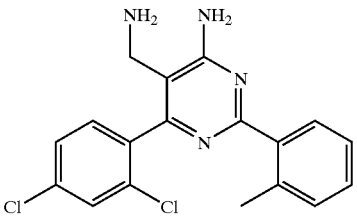

The title compound, MS: m/e=358.9 (M+H$^+$), was prepared from 2-methyl-benzamidine and 2-(2,4-dichloro-benzylidene)-malononitrile in analogy to the process described in Example 11 as a solid.

Example 53

5-Aminomethyl-2-(3,5-bis-trifluoromethyl-phenyl)-6-(2,4-dichloro-phenyl)-pyrimidin-4-ylamine

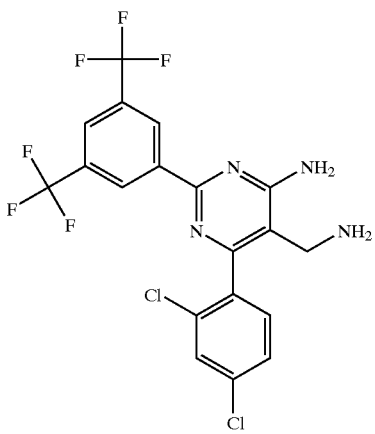

The title compound, MS: m/e=481.2 (M+H$^+$), was prepared from 3,5-bis-trifluoromethyl-benzamidine and 2-(2,4-dichloro-benzylidene)-malononitrile in analogy to the process described in Example 11 as a solid.

Example 54

5-Aminomethyl-6-(2,4-dichloro-phenyl)-2-(4-fluoro-phenoxymethyl)-pyrimidin-4-ylamine

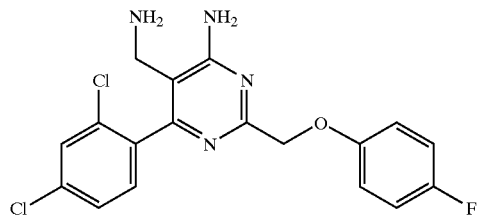

The title compound, MS: m/e=392.8 (M+H$^+$), was prepared from 2-(4-fluoro-phenoxy)-acetamidine and 2-(2,4-dichloro-benzylidene)-malononitrile in analogy to the process described in Example 11 as a solid.

Example 55

5-Aminomethyl-6-(2-chloro-phenyl)-2-phenyl-pyrimidin-4-ylamine

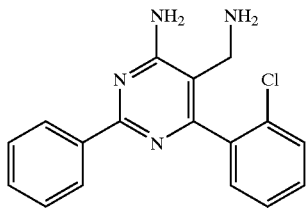

The title compound, MS: m/e=311.0 (M$^+$), was prepared from 2-(2-chloro-benzylidene)-malononitrile in analogy to the process described in Example 11 as a solid.

Example 56

5-Aminomethyl-6-(2-bromo-phenyl)-2-phenyl-pyrimidin-4-ylamine

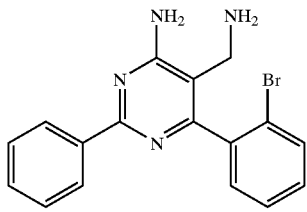

The title compound, MS: m/e=354.8 (M$^+$), was prepared from 2-(2-bromo-benzylidene)-malononitrile in analogy to the process described in Example 11 as a solid.

Example 57

5-Aminomethyl-2-dibenzofuran-2-yl-6-(2,4-dichloro-phenyl)-pyrimidin-4-ylamine

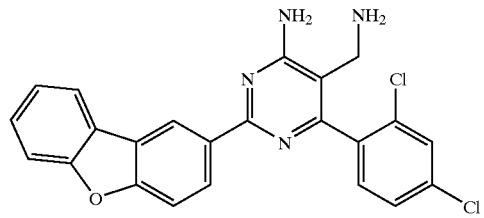

The title compound, MS: m/e=434.9 (M$^+$), was prepared from dibenzofuran-2-carboxamidine and 2-(2,4-dichloro-benzylidene)-malononitrile in analogy to the process described in Example 11 as a solid.

Example 58

5-Aminomethyl-6-(2,4-bis-trifluoromethyl-phenyl)-2-phenyl-pyrimidin-4-ylamine

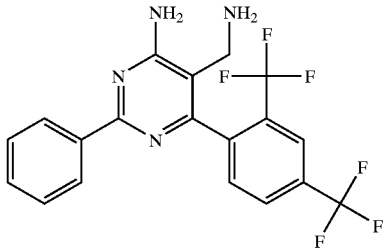

The title compound, MS: m/e=413.0 (M+H$^+$), was prepared from 2-(2,4-bis-trifluoromethyl-benzylidene)-malononitrile in analogy to the process described in Example 11 as a solid.

Example 59

5-Aminomethyl-6-(2-fluoro-4-methoxy-phenyl)-2-phenyl-pyrimidin-4-ylamine

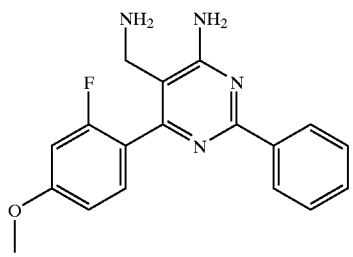

The title compound, MS: m/e=324.8 (M$^+$), was prepared from 2-(2-fluoro-4-methoxy-benzylidene)-malononitrile in analogy to the process described in Example 11 as a solid.

Example 60

5-Aminomethyl-6-(2,4-dimethoxy-phenyl)-2-phenyl-pyrimidin-4-ylamine

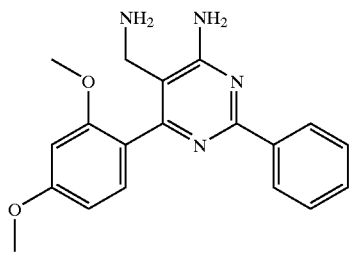

The title compound, MS: m/e=336.8 (M$^+$), was prepared from 2-(2,4-dimethoxy-benzylidene)-malononitrile in analogy to the process described in Example 11 as a solid.

Example 61

5-Aminomethyl-2-(1H-indol-2-yl)-6-phenyl-pyrimidin-4-ylamine

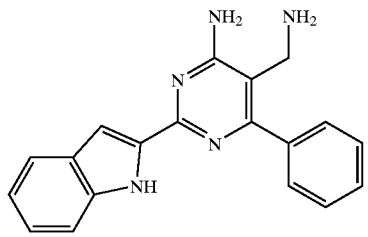

The title compound, MS: m/e=315.8 (M+H$^+$), was prepared from 1H-indole-2-carboxamidine and 2-benzylidene-malononitrile in analogy to the process described in Example 11 as a solid.

Example 62

5-Aminomethyl-6-benzo[1,3]dioxol-5-yl-2-cyclopropyl-pyrimidin-4-ylamine

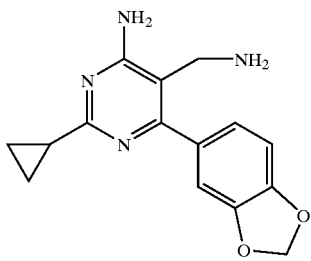

The title compound, MS: m/e=284.7 (M+H$^+$), was prepared from cyclopropylcarboxamidine and 2-benzo[1,3]dioxol-5-ylmethylene-malononitrile in analogy to the process described in Example 11 as a solid.

Example 63

5-Aminomethyl-6-(2-fluoro-phenyl)-2-phenyl-pyrimidin-4-ylamine

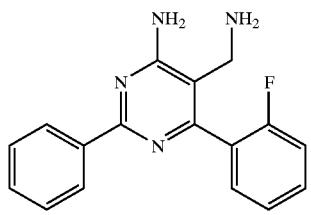

The title compound, MS: m/e=294.9 (M+H$^+$), was prepared from 2-(2-fluoro-benzylidene)-malononitrile in analogy to the process described in Example 11 as a solid.

Example 64

5-Aminomethyl-2-phenyl-6-(2-trifluoromethyl-phenyl)-pyrimidin-4-ylamine

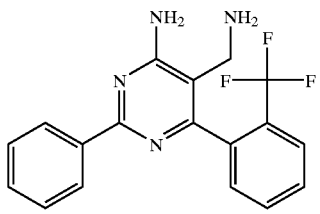

The title compound, MS: m/e=345.1 (M+H$^+$), was prepared from 2-(2-trifluoromethyl-benzylidene)-malononitrile in analogy to the process described in Example 11 as a solid.

Example 65

5-Aminomethyl-2-benzofuran-2-yl-6-phenyl-pyrimidin-4-ylamine

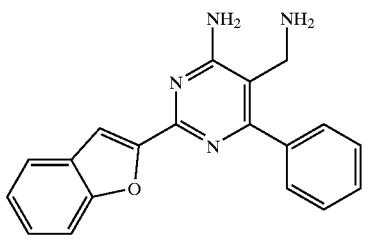

The title compound, MS: m/e=316.7 (M+H$^+$), was prepared from benzofuran-2-carboxamidine and 2-benzylidene-malononitrile in analogy to the process described in Example 11 as a solid.

Example 66

5-Aminomethyl-6-(4-fluoro-phenyl)-2-phenyl-pyrimidin-4-ylamine

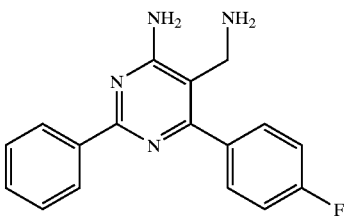

The title compound, MS: m/e=294.8 (M+H$^+$), was prepared from 2-(4-fluoro-benzylidene)-malononitrile in analogy to the process described in Example 11 as a solid.

Example 67

5-Aminomethyl-2-(3,4-dimethoxy-phenyl)-6-phenyl-pyrimidin-4-ylamine

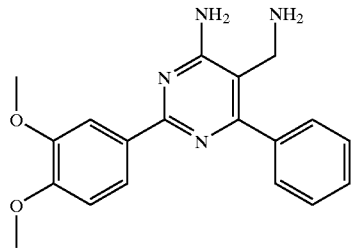

The title compound, MS: m/e=336.8 (M+H⁺), was prepared from 3,4-dimethoxybenzamidine and 2-benzylidene-malononitrile in analogy to the process described in Example 11 as a solid.

Example 68

5-Aminomethyl-6-phenyl-2-pyridin-4-yl-pyrimidin-4-ylamine

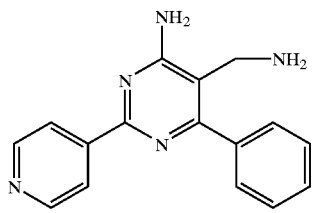

The title compound, MS: m/e=278.0 (M+H⁺), was prepared from isonicotinamidine and 2-benzylidene-malononitrile in analogy to the process described in Example 11 as a solid.

Example 69

5-Aminomethyl-6-(3-chloro-phenyl)-2-phenyl-pyrimidin-4-ylamine

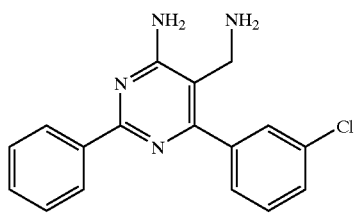

The title compound, MS: m/e=31.0 (M+H⁺), was prepared from 2-(3-chloro-benzylidene)-malononitrile in analogy to the process described in Example 11 as a solid.

Example 70

5-Aminomethyl-6-phenyl-2-thiophen-2-yl-pyrimidin-4-ylamine

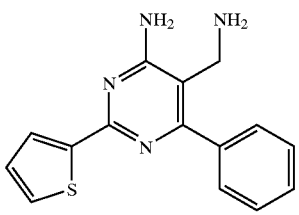

The title compound, MS: m/e=282.8 (M+H⁺), was prepared from thiophene-2-carboxamidine and 2-benzylidene-malononitrile in analogy to the process described in Example 11 as a solid.

Example 71

5-Aminomethyl-6-(3-fluoro-phenyl)-2-phenyl-pyrimidin-4-ylamine

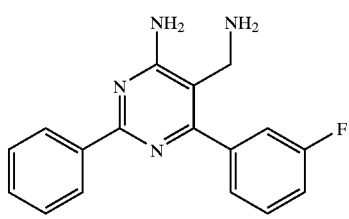

The title compound, MS: m/e=294.8 (M+H⁺), was prepared from 2-(3-fluoro-benzylidene)-malononitrile in analogy to the process described in Example 11 as a solid.

Example 72

5-Aminomethyl-2,6-diphenyl-pyrimidin-4-ylamine

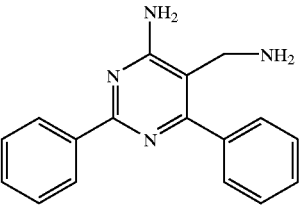

The title compound, MS: m/e=276.9 (M+H⁺), was prepared from 2-benzylidene-malononitrile in analogy to the process described in Example 11 as a solid.

Example 73

5-Aminomethyl-6-(4-methoxy-phenyl)-2-phenyl-pyrimidin-4-ylamine

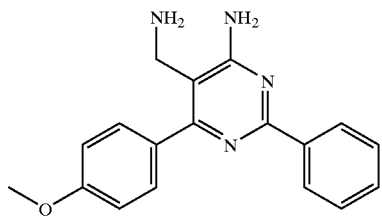

The title compound, MS: m/e=306.9 (M+H⁺), was prepared from 2-(4-metoxy-benzylidene)-malononitrile in analogy to the process described in Example 11 as a solid.

Example 74

5-Aminomethyl-2-phenyl-6-thiophen-3-yl-pyrimidin-4-ylamine

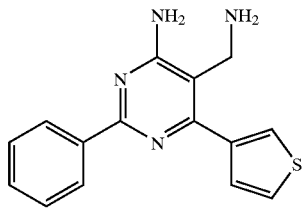

The title compound, MS: m/e=283.0 (M+H⁺), was prepared from 2-thiophen-3-ylmethylene-malononitrile in analogy to the process described in Example 11 as a solid.

Example 75

5-Aminomethyl-6-(3-methoxy-phenyl)-2-phenyl-pyrimidin-4-ylamine

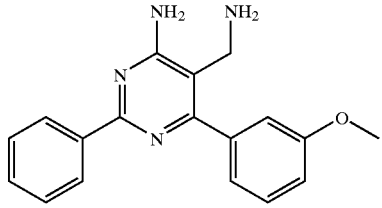

The title compound, MS: m/e=307.2 (M+H⁺), was prepared from 4-Amino-6-(3-methoxy-phenyl)-2-phenyl-pyrimidine-5-carbonitrile in analogy to the process described in Example 11 as a solid.

Example 76

(Procedure 6 in Reaction Scheme I) 6-(2,4-Dichloro-phenyl)-5-methylaminomethyl-2-phenyl-pyrimidin-4-ylamine

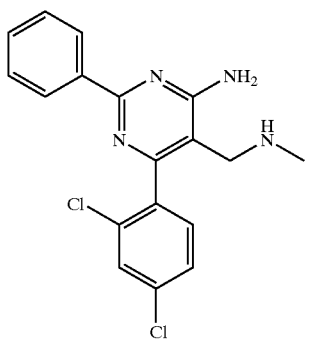

Under an atmosphere of argon, 9-BBN (0.348 ml of a 0.5molar solution in hexane, 0.174 mmol) was added to a solution of 4-amino-6-(2,4-dichloro-phenyl)-2-phenyl-pyrimidine-5-carbonitrile (60 mg, 0.174 mmol) in THF (1 ml) and stirred for 2.5 h at r.t. Potassium-tert-butylate (20 mg, 0.174 mmol) was added, followed by a drop of Methyl iodide after 10 min. The mixture was stirred overnight, then ethanolamine (11 mg, 0.174 mmol) was added and the mixture was heated to 50° C. for 3 h. After cooling, the mixture was filtered, and the filtrate was evaporated. Purification of the re-dissolved (DMF, 1 ml) residue by automated, preparative HPLC (YMC CombiPrep C18 column 50×20 mm, solvent gradient 5–95% CH₃CN in 0.1% TFA(aq) over 6.0 min, λ=230 nm, flow rate 40 ml/min) gave the title compound, MS: m/e=358.9 (M+H⁺), (12 mg, 19%) as a foam.

Example 77

Synthesis of 2-Amino-nicotinonitriles (Procedure 7 in Reaction Scheme II) 2-Amino-4-(2,4-dichloro-phenyl)-6-phenyl-nicotinonitrile A mixture of 2-(2,4-dichloro-benzylidene)-malononitrile (1.125 g, 5 mmol), acetophenone (601 mg, 5 mmol), ammonium acetate (578 mg, 7.5 mmol), and toluene (5 ml) was stirred for 3 h at reflux. Upon cooling to room temperature, the mixture was taken up in ethyl acetate and extracted with satd. NaHCO₃, water, and satd. NaCl, and dried over Na₂SO₄. The solvent was then evaporated and the title compound (600 mg, 35%), MS: m/e=339.5 (M+H⁺), was isolated from the residue by column chromatography (silica gel, hexanes, ethyl acetate).

¹H-NMR (300 MHz, CDCl₃, 25° C.): δ(ppm) 5.38 (2H, bs), 7.13 (1H, s), 7.30–7.58 (6H, m), 7.95–8.02 (2H, m).

The following 2-amino-nicotinonitrile was prepared in analogy to the procedure described above:

2-Amino-4-(2,4-dichloro-phenyl)-5-methyl-6-phenyl-nicotinonitrile, MS: m/e=353.9 (M+H⁺), was prepared from propiophenone as a solid (425 mg, 24%).

Example 78

Synthesis of 3-Aminomethyl-pyridin-2-ylamines (Procedure 8 in Reaction Scheme II) 3-Aminomethyl-4-(2,4-dichloro-phenyl)-6-phenyl-pyridin-2-ylamine

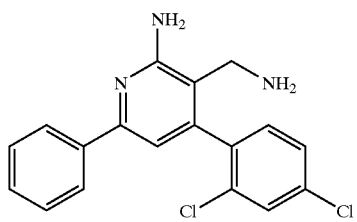

Under an atmosphere of argon, a solution of 2-amino-4-(2,4-dichloro-phenyl)-6-phenyl-nicotinonitrile (580 mg, 1.71 mmol) in THF (2 ml) is added slowly to a suspension of LiAlH$_4$ (324 mg, 8.52 mmol) in THF (2 ml). After stirring for 2 h at room temperature, the reaction mixture is cooled to −20° C. and water (0.4 ml) is added. After 15 min, ethyl acetate is added and the mixture is filtered through Decalite. The organic phase is then separated, washed with water, and dried over sodium sulfate. Purification by flash chromatography (silica gel, methanol, dichloromethane) affords the title compound, MS: m/e=343.8 (M+H$^+$), as a light yellow solid (36 mg, 6%).

$^1$H-NMR (300 MHz, CDCl$_3$, 25° C.): δ(ppm)=3.40 (1H, d, J=10 Hz), 3.59 (1H, d, J=10 Hz), 6.49 (2H, bs), 6.90 (1H, s), 7.30–7.55 (5H, m), 7.57 (1H, s), 7.90–8.10 (2H, m)

Example 79

3-Aminomethyl-4-(2,4-dichloro-phenyl)-5-methyl-6-phenyl-pyridin-2-ylamine

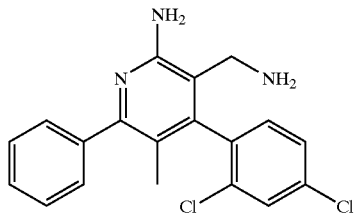

The title compound, MS: m/e=357.9 (M$^+$), was prepared from 2-amino-4-(2,4-dichloro-phenyl)-5-methyl-6-phenyl-nicotinonitrile in analogy to the process described in Example 78 as a solid (22 mg, 9%).

Example 80

High-Throughput Reduction of carbonitriles to aminomethyl Compounds (Procedure 9 in Reaction Schemes I and II)

[5-Aminomethyl-6-(4-chloro-phenyl)-2-pyridin-3-yl-pyrimidin-4-yl]-methyl-amine

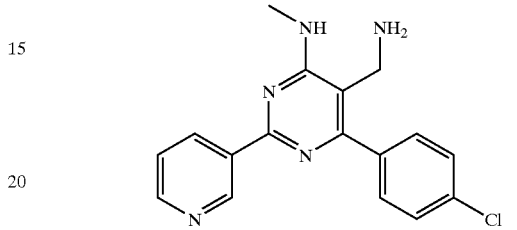

High-Throughput Reduction of carbonitriles to aminomethyl compounds 4-(4-Chlorophenyl)-6-(dimethylamino)-2-(3-pyridinyl)-5-pyrimidinecarbonitrile (Bionet) (50 mg, 0.155 mmol) was dissolved in THF (1 ml) and added, under an atmosphere of argon, to a cooled (0° C.) suspension of 100 mg of Lithium aluminium hydride in 1 ml THF in a reaction vial. The reaction mixture was shaken first for 2 h at r.t. and subsequently for 4 h at 40° C. Upon cooling, water was added carefully and the mixture was filtered. The filtrate was evaporated in a vacuum zentrifuge (45° C.). Purification of the re-dissolved (DMF, 1 ml) residue by automated, preparative HPLC (YMC CombiPrep C18 column 50×20 mm, solvent gradient 5–95% CH$_3$CN in 0.1% TFA(aq) over 6.0 min, λ=230 nm, flow rate 40 ml/min) gave 17 mg (34%) of the title compound, MS: m/e=326.0 (M+H$^+$), as a solid.

Example 81

5-Aminomethyl-6-benzo[1,3]dioxol-5-yl-2-(4-methoxy-phenyl)-pyrimidin-4-ylamine

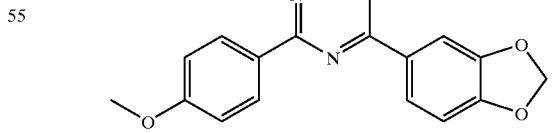

The title compound, MS: m/e=351.0 (M+H$^+$), was prepared in analogy to the process described in Example 80 from 4-amino-6-benzo[1,3]dioxol-5-yl-2-(4-methoxy-phenyl)-pyrimidine-5-carbonitrile.

Example 82

5-Aminomethyl-6-benzo[1,3]dioxol-5-yl-2-phenyl-pyrimidin-4-ylamine

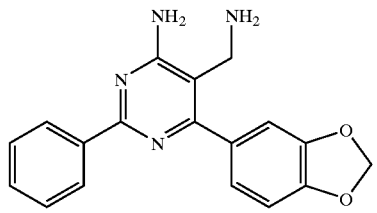

The title compound, MS: m/e=321.0 (M+H⁺), was prepared in analogy to the process described in Example 80 from 4-amino-6-benzo[1,3]dioxol-5-yl-2-phenyl-pyrimidine-5-carbonitrile.

Example 83

[5-Aminomethyl-6-(4-chloro-phenyl)-2-pyridin-3-yl-pyrimidin-4-yl]-isopropyl-amine

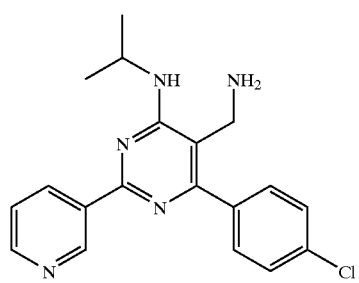

The title compound, MS: m/e=354.1 (M+H⁺), was prepared in analogy to the process described in Example 80 from 4-(4-chlorophenyl)-6-(isopropylamino)-2-(3-pyridinyl)-5-pyrimidinecarbonitrile.

Example 84

(5-Aminomethyl-2,6-diphenyl-pyrimidin-4-yl)-methyl-amine

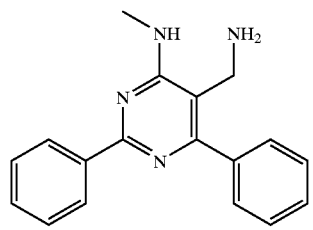

The title compound, MS: m/e=290.9 (M+H⁺), was prepared in analogy to the process described in Example 80 from 4-(methylamino)-2,6-diphenyl-5-pyrimidinecarbonitrile (Bionet).

Example 85

3-Aminomethyl-4-(4-chloro-phenyl)-5-methyl-6-phenyl-pyridin-2-ylamine

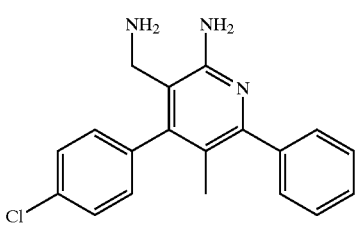

The title compound, MS: m/e=323.9 (M+H⁺), was prepared in analogy to the process described in Example 80 from 2-amino-4-(4-chlorophenyl)-5-methyl-6-phenylnicotinonitrile (Bionet).

Example 86

3-Aminomethyl-4-(4-chloro-phenyl)-6-phenyl-pyridin-2-ylamine

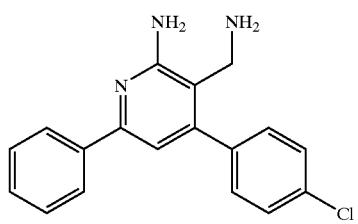

The title compound, MS: m/e=310.3 (M+H⁺), was prepared in analogy to the process described in Example 80 from 2-amino-4-(4-chlorophenyl)-6-phenylnicotinonitrile (Bionet).

Example 87

3-Aminomethyl-4,6-bis-(4-fluoro-phenyl)-pyridin-2-ylamine

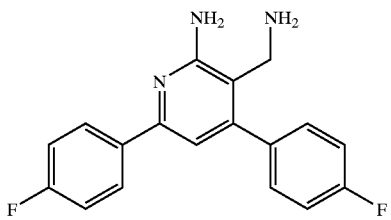

The title compound, MS: m/e=311.9 (M+H⁺), was prepared in analogy to the process described in Example 80 from 2-amino-4,6-bis(4-fluorophenyl)nicotinonitrile (Bionet).

Example 88

(Procedure 10 in Reaction Scheme II) 3-Aminomethyl-4-benzo[1,3]dioxol-5-yl-6-phenyl-pyridin-2-ylamine

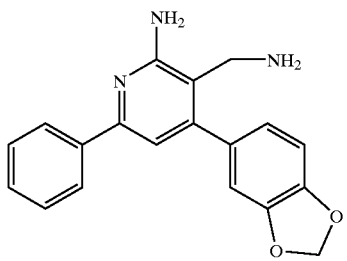

2-Benzo[1,3]dioxol-5-ylmethylene-malononitrile (79 mg, 0.4 mmol), benzophenone (48 mg, 0.4 mmol), ammonium acetate (78 mg, 1.2 mmol), and toluene (4 ml) were placed in a reaction vial and shaken overnight at 118° C. Upon cooling and filtration, the solution was evaporated in a vacuum zentrifuge (45° C.) and the residue was purified by automated, preparative HPLC (YMC CombiPrep C18 column 50×20 mm, solvent gradient 5–95% $CH_3CN$ in 0.1% TFA(aq) over 6.0 min, λ=230 nm, flow rate 40 ml/min). The obtained solid (28 mg) was dissolved in THF (1 ml) and added, under an atmosphere of argon, to a cooled (0° C.) suspension of 100 mg of lithium aluminium hydride in 1 ml THF in a reaction vial. The reaction mixture was shaken first for 2 h at r.t. and subsequently for 4 h at 40° C. Upon cooling, water was added carefully and the mixture was filtered. The filtrate was evaporated in a vacuum zentrifuge (45° C.). Purification of the re-dissolved (DMF, 1 ml) residue by automated, preparative HPLC (YMC CombiPrep C18 column 50×20 mm, solvent gradient 5–95% $CH_3CN$ in 0.1% TFA(aq) over 6.0 min, λ=230 nm, flow rate 40 ml/min) gave 11 mg (7%) of the title compound, MS: m/e=320.1 ($M+H^+$), as a solid.

Example 89

The following tests were carried out in order to determine the activity of the compounds of formula I.

Activity of DPP-IV inhibitors are tested with natural human DPP-IV derived from a human plasma pool or with recombinant human DPP-IV. Human citrate plasma from different donors is pooled, filtered through a 0.2 micron membrane under sterile conditions, and aliquots of 1 ml are shock frozen and stored at −120° C. until used. In the calorimetric DPP-IV assay 5 to 10 μl human plasma, and in the fluorometric assay 1.0 μl of human plasma in a total assay volume of 100 μl is used as an enzyme source. The cDNA of the human DPP-IV sequence of amino acid 31- to 766, restricted for the N-terminus and the transmembrane domain, is cloned into pichia pastoris. The sequence is available under Accession Number NM_001935. It is also disclosed, for example, in Misumi et al. (1992), Molecular cloning and sequence analysis of human dipeptidyl peptidase IV, a serine proteinase of the cell surface. Biochim. Biophys. Acta 1131(3), 333–336. Human DPP-IV is expressed and purified from the culture medium using conventional column chromatography including size exclusion and anion and cation chromatography. The purity of the final enzyme preparation of Coomassie blue SDS-PAGE is >95%. In the calorimetric DPP-IV assay 20 ng rec.-h DPP-IV and in the fluorometric assay 2 ng rec-h DPP-IV in a total assay volume of 100 μl is used as an enzyme source.

In the fluorogenic assay Ala-Pro-7-amido-4-trifluoromethylcoumarin (Calbiochem No 125510) is used as a substrate. A 20 mM stock solution in 10 % $DMF/H_2O$ is stored at −20° C. until use. In IC50 determinations a final substrate concentration of 50 μM is used. In assays to determine kinetic parameters as Km, Vmax, Ki, the substrate concentration is varied between 10 μM and 500 μM.

In the colorimetric assay H-Ala-Pro-pNA.HCl (Bachem L-1115) is used as a substrate. A 10 mM stock solution in 10% $MeOH/H_2O$ is stored at −20° C. until use. In IC50 determinations a final substrate concentration of 200 μM is used. In assays to determine kinetic parameters as Km, Vmax, Ki, the substrate concentration is varied between 100 μM and 2000 μM.

Fluorescence is detected in a Perkin Elmer Luminescence Spectrometer LS 50B at an excitation wavelength of 400 nm and an emission wavelength of 505 nm continuously every 15 seconds for 10 to 30 minutes. Initial rate constants are calculated by best fit linear regression.

The absorption of pNA, i.e., para-nitroanilin, liberated from the colorimetric substrate is detected in a Packard SpectraCount at 405 nM continuously every 2 minutes for 30 to 120 minutes. Initial rate constants are calculated by best fit linear regression.

DPP-IV activity assays are performed in 96 well plates at 37° C. in a total assay volume of 100 μl. The assay buffer consists of 50 mM Tris/HCl pH 7.8 containing 0.1 mg/ml BSA and 100 mM NaCl. Test compounds are solved in 100 % DMSO, diluted to the desired concentration in 10% $DMSO/H_2O$. The final DMSO concentration in the assay is 1% (v/v). At this concentration enzyme inactivation by DMSO is <5%. Compounds are with (10 minutes 37° C.) and without preincubation with the enzyme. Enzyme reaction are started with substrate application followed by immediate mixing.

IC50 determinations of test compounds are calculated by non-linear best fit regression of the DPP-IV inhibition of at least 5 different compound concentrations. Kinetic parameters of the enzyme reaction are calculated at least 5 different substrate concentrations and at least 5 different test compound concentrations.

The preferred compounds of the present invention exhibit IC50 values of 1 nM to 10 μM, more preferably of 1–100 nM, as shown in the following table:

| Example | $IC_{50}$ [μM] |
| --- | --- |
| 76 | 0.391 |
| 13 | 0.0002 |
| 12 | 0.0001 |
| 23 | 0.013 |
| 20 | 0.003 |
| 43 | 0.389 |
| 11 | 0.172 |
| 16 | 0.0007 |
| 79 | 0.873 |

Example 90

Galenical Examples

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatine capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatine capsule | |
| Gelatine | 75.0 mg |
| Glycerol 85% | 32.0 mg |
| Karion 83 | 8.0 mg |
| | (dry matter) |
| Titan dioxide | 0.4 mg |
| Iron oxide yellow | 1.1 mg |

The active ingredient is dissolved in a warm melting of the other ingredients and the mixture is filled into soft gelatine capsules of appropriate size. The filled soft gelatine capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with magnesium stearate and the flavouring additives and filled into sachets.

What is claimed is:

1. A compound of formula (I)

wherein
X is N;
$R^1$ and $R^2$ are independently hydrogen or lower alkyl;
$R^3$ is heterocyclyl; heterocyclyl mono-, di-, or tri-substituted, independently, by lower alkyl, lower alkoxy, perfluoro-lower alkyl, amino or halogen; aryl; or aryl mono-, di-, or tri-substituted, independently, by halogen, lower alkyl, lower alkoxy, amino or perfluoro-lower alkyl;
$R^4$ is lower alkyl; ethoxy, propoxy, isoproxy, butoxy, isobutoxy or hexyloxy; lower alkylthio; heterocyclyl;

heterocyclyl mono-, di-, or tri-substituted, independently, by lower alkyl, lower alkoxy, perfluoro-lower alkyl, amino or halogen; aryl; aryl mono-, di-, or tri-substituted, independently, by lower alkyl, lower alkoxy, halogen, amino, or perfluoro-lower alkyl; aryloxy lower alkyl or cycloalkyl;

$R^5$ is hydrogen or lower alkyl;

or a pharmaceutically acceptable salts thereof.

2. The compound according to claim 1, wherein $R^1$ is hydrogen.

3. The compound according to claim 1, wherein $R^2$ is hydrogen.

4. The compound according to claim 1, wherein $R^3$ is heterocyclyl or substituted heterocyclyl, wherein the heterocyclic residue is selected from pyridyl, pyrimidinyl, furyl, thienyl, indolyl, benzo[1,3]dioxolyl, benzofuranyl, benzothiophenyl, dibenzofuranyl, oxazolyl, imidazolyl, thiazolyl, isoxazolyl, pyrazolyl, isothiazolyl, oxadiazolyl, thiadiazolyl, triazolyl, tetrazolyl, oxatriazolyl, thiatriazolyl, pyridazyl, pyrimidinyl, pyrazinyl, pyrrolidinyl, azepanyl, and morpholino, and wherein substituted heterocyclyl is said heterocyclic residue which is mono-, di- or tri-substituted, independently, by halogen, amino, perfluoro-lower alkyl, lower alkyl or lower alkoxy.

5. The compound according to claim 4, wherein $R^3$ is unsubstituted thienyl or unsubstituted benzo[1,3]dioxolyl.

6. The compound according to claim 1, wherein $R^3$ is aryl which is phenyl; or substituted aryl which is phenyl ortho-, meta- or para-substituted, independently, by lower alkyl, lower alkoxy, halogen, amino or perfluoro-lower alkyl.

7. The compound according to claim 6, wherein $R^3$ is 2,4-dichloro-phenyl.

8. The compound according to claim 1, wherein $R^4$ is aryl which is phenyl; or substituted aryl which is phenyl ortho-, meta- and/or para-substituted, independently, by halogen, amino, lower alkyl, perfluoro-lower alkyl or lower alkoxy.

9. The compound according to claims 1, wherein $R^4$ is lower alkoxy.

10. The compound according to claim 1, wherein $R^4$ is lower alkylthio.

11. The compound according to claim 1, wherein $R^4$ is heterocyclyl or substituted heterocyclyl, wherein the heterocyclic residue is selected from pyridyl, thienyl, indolyl, benzo[1,3]dioxolyl, benzofuranyl, benzothiophenyl, dibenzofuranyl, pyrrolidinyl, azepanyl and morpholino, and wherein substituted heterocyclyl is said heterocyclic residue which is mono-, di- or tri-substituted, independently, by halogen, amino, perfluoro-lower alkyl, lower alkyl or lower alkoxy.

12. The compound according to claim 1, wherein X is N; $R^1$ and $R^2$ are hydrogen;

$R^3$ is 2,4-dichloro-phenyl; and $R^4$ is methoxy, methylthio, heterocyclyl selected from pyrrolidinyl and azepanyl, or aryl which is phenyl, or substituted aryl which is phenyl ortho-, meta- and/or para-substituted, independently, by fluoro, methyl or methoxy.

13. The compound according to claim 1, wherein X is N; $R^1$ is hydrogen or lower alkyl;

$R^2$ is hydrogen or lower alkyl;

$R^3$ is unsubstituted thienyl, unsubstituted benzo[1,3]dioxolyl, or phenyl or substituted phenyl which is ortho-, meta- or para-substituted, independently, by lower alkyl, lower alkoxy, halogen or perfluoro-lower alkyl;

$R^4$ is lower alkyl, ethoxy, propoxy, isopropoxy, butoxy, isobutoxy or hexyloxy, lower alkylthio, $C_{3-6}$-cycloalkyl, heterocyclyl or substituted heterocyclyl wherein the heterocyclic residue is selected from pyridyl, thienyl, indolyl, benzo[1,3]dioxolyl, benzofuranyl, benzothiophenyl, dibenzofuranyl, pyrrolidinyl, azepanyl and morpholino, and wherein substituted heterocyclyl is said heterocyclic residue which is mono- or di-substituted, independently, by lower alkyl or lower alkoxy, a naphthyl residue which is mono-substituted by lower alkoxy, a phenyl or substituted phenyl residue which is ortho-, meta- or para-substituted, independently, by halogen, amino, lower alkyl, perfluoro-lower alkyl or lower alkoxy, or phenoxy lower alkyl, wherein the phenyl residue is substituted by halogen, and $R^5$ is hydrogen or lower alkyl.

14. The compound according to claim 1, selected from the group consisting of:

5-Aminomethyl-6-(2,4-dichloro-phenyl)-2-phenyl-pyrimidin-4-ylamine,

5-Aminomethyl-2-phenyl-6-p-tolyl-pyrimidin-4-ylamine,

5-Aminomethyl-6-(2,4-dichloro-phenyl)-2-(3-methoxy-phenyl)-pyrimidin-4-ylamine,

5-Aminomethyl-2-phenyl-6-o-tolyl-pyrimidin-4-ylamine,

5-Aminomethyl-6-(2,4-difluoro-phenyl)-2-phenyl-pyrimidin-4-ylamine,

5-Aminomethyl-6-(2,4-dichloro-phenyl)-2-m-tolyl-pyrimidin-4-ylamine,

5-Aminomethyl-6-(2,4-dichloro-phenyl)-2-(3,4,5-trimethoxy-phenyl)-pyrimidin-4-ylamine, 5-Aminomethyl-6-(2,4-dimethyl-phenyl)-2-phenyl-pyrimidin-4-ylamine, 5-Aminomethyl-6-(2,4-dichloro-phenyl)-2-(3,5-dimethoxy-phenyl)-pyrimidin-4-ylamine, 5-Aminomethyl-6-(2,4-dichloro-phenyl)-2-(3-fluoro-phenyl)-pyrimidin-4-ylamine, 5-Aminomethyl-6-(2,4-dichloro-phenyl)-2-(4-fluoro-phenyl)-pyrimidin-4-ylamine, 5-Aminomethyl-6-(2,4-dichloro-phenyl)-2-(4-methoxy-1-methyl-1H-indol-6-yl)-pyrimidin-4-ylamine, 5-Aminomethyl-2-benzofuran-2-yl-6-(2,4-dichloro-phenyl)-pyrimidin-4-ylamine, 5-Aminomethyl-6-(2,4-dichloro-phenyl)-2-(1H-indol-2-yl)-pyrimidin-4-ylamine, 5-Aminomethyl-6-(2,4-dichloro-phenyl)-2-m-tolyl-pyrimidin-4-ylamine, 2-(4-Amino-3-methoxy-phenyl)-5-aminomethyl-6-(2,4-dichloro-phenyl)-pyrimidin-4-ylamine, 5-Aminomethyl-2-azepan-1-yl-6-(2,4-dichloro-phenyl)-pyrimidin-4-ylamine, 5-Aminomethyl-6-(2,4-dichloro-phenyl)-2-(3,4-difluoro-phenyl)-pyrimidin-4-ylamine, 5-Aminomethyl-6-(2,4-dichloro-phenyl)-2-pyrrolidin-1-yl-pyrimidin-4-ylamine, 5-Aminomethyl-6-(2,4-dichloro-phenyl)-2-methylsulfanyl-pyrimidin-4-ylamine, 5-Aminomethyl-6-(2,4-dichloro-phenyl)-2-(3,4-dimethoxy-phenyl)-pyrimidin-4-ylamine, 5-Aminomethyl-6-(2,4-dichloro-phenyl)-2-thiophen-2-yl-pyrimidin-4-ylamine, 5-Aminomethyl-6-(2,4-dichloro-phenyl)-2-(2-fluoro-phenyl)-pyrimidin-4-ylamine, 5-Aminomethyl-2-(4-chloro-phenyl)-6-(2,4-dichloro-phenyl)-pyrimidin-4-ylamine,
5-Aminomethyl-6-(2,4-dichloro-phenyl)-2-methoxy-pyrimidin-4-ylamine,
5-Aminomethyl-2-cyclopropyl-6-pheny-pyrimidin-4-ylamine5-Aminomethyl-6-(2,4-dichloro-phenyl)-2-p-tolyl-pyrimidin-4-ylamine,
5-Aminomethyl-6-(2,4-dichloro-phenyl)-2-(4-methoxy-phenyl)-pyrimidin-4-ylamine,
5-Aminomethyl-2-benzo[1,3]dioxol-5-yl-6-(2,4-dichloro-phenyl)-pyrimidin-4-ylamine,
5-Aminomethyl-6-(2,4-dichloro-phenyl)-2-(3-trifluoromethyl-phenyl)-pyrimidin-4-ylamine,
5-Aminomethyl-6-(2,4-dichloro-phenyl)-2-morpholin-4-yl-pyrimidin-4-ylamine,
5-Aminomethyl-6-(2,4-dichloro-phenyl)-2-(4-trifluoromethyl-phenyl)-pyrimidin-4-ylamine,
5-Aminomethyl-2-(3-chloro-phenyl)-6-(2,4-dichloro-phenyl)-pyrimidin-4-ylamine,
5-Aminomethyl-6-(2,4-dichloro-phenyl)-2-methyl-pyrimidin-4-ylamine,
5-Aminomethyl-6-(2,4-dichloro-phenyl)-2-naphthalen-2-yl-pyrimidin-4-ylamine,
5-Aminomethyl-6-(2,4-dichloro-phenyl)-2-naphthalen-1-yl-pyrimidin-4-ylamine,
5-Aminomethyl-6-(2,4-dichloro-phenyl)-2-(3-methoxy-phenyl)-pyrimidin-4-ylamine,
5-Aminomethyl-6-(2,4-dichloro-phenyl)-2-(3,5-difluoro-phenyl)-pyrimidin-4-ylamine,
5-Aminomethyl-6-(2,4-dichloro-phenyl)-2-(2-methoxy-phenyl)-pyrimidin-4-ylamine,
5-Aminomethyl-6-(4-ethyl-phenyl)-2-phenyl-pyrimidin-4-ylamine,
5-Aminomethyl-6-(2,4-dichloro-phenyl)-2-isopropyl-pyrimidin-4-ylamine,
5-Aminomethyl-2-(2-chloro-4-fluoro-phenyl)-6-(2,4-dichloro-phenyl)-pyrimidin-4-ylamine,
5-Aminomethyl-2-benzo[b]thiophen-2-yl-6-(2,4-dichloro-phenyl)-pyrimidin-4-ylamine,
5-Aminomethyl-6-(2,4-dichloro-phenyl)-2-(6-methoxy-naphthalen-2-yl)-pyrimidin-4-ylamine,
5-Aminomethyl-2-phenyl-6-m-tolyl-pyrimidin-4-ylamine,
5-Aminomethyl-6-(4-chloro-phenyl)-2-phenyl-pyrimidin-4-ylamine,
5-Aminomethyl-2-phenyl-6-(4-trifluoromethyl-phenyl)-pyrimidin-4-ylamine,
5-Aminomethyl-6-(2-methoxy-phenyl)-2-phenyl-pyrimidin-4-ylamine,
5-Aminomethyl-6-(2,4-dichloro-phenyl)-2-o-tolyl-pyrimidin-4-ylamine,
5-Aminomethyl-2-(3,5-bis-trifluoromethyl-phenyl)-6-(2,4-dichloro-phenyl)-pyrimidin-4-ylamine,
5-Aminomethyl-6-(2,4-dichloro-phenyl)-2-(4-fluoro-phenoxymethyl)-pyrimidin-4-ylamine,
5-Aminomethyl-6-(2-chloro-phenyl)-2-phenyl-pyrimidin-4-ylamine,
5-Aminomethyl-6-(2-bromo-phenyl)-2-phenyl-pyrimidin-4-ylamine,
5-Aminomethyl-2-dibenzofuran-2-yl-6-(2,4-dichloro-phenyl)-pyrimidin-4-ylamine,
5-Aminomethyl-6-(2,4-bis-trifluoromethyl-phenyl)-2-phenyl-pyrimidin-4-ylamine,
5-Aminomethyl-6-(2-fluoro-4-methoxy-phenyl)-2-phenyl-pyrimidin-4-ylamine,
5-Aminomethyl-6-(2,4-dimethoxy-phenyl)-2-phenyl-pyrimidin-4-ylamine,
5-Aminomethyl-2-(1H-indol-2-yl)-6-phenyl-pyrimidin-4-ylamine,
5-Aminomethyl-6-benzo[1,3]dioxol-5-yl-2-cyclopropyl-pyrimidin-4-ylamine,
5-Aminomethyl-6-(2-fluoro-phenyl)-2-phenyl-pyrimidin-4-ylamine,
5-Aminomethyl-2-phenyl-6-(2-trifluoromethyl-phenyl)-pyrimidin-4-ylamine,
5-Aminomethyl-2-benzofuran-2-yl-6-phenyl-pyrimidin-4-ylamine,
5-Aminomethyl-6-(4-fluoro-phenyl)-2-phenyl-pyrimidin-4-ylamine,
5-Aminomethyl-2-(3,4-dimethoxy-phenyl)-6-phenyl-pyrimidin-4-ylamine,
5-Aminomethyl-6-phenyl-2-pyridin-4-yl-pyrimidin-4-ylamine,
5-Aminomethyl-6-(3-chloro-phenyl)-2-phenyl-pyrimidin-4-ylamine,
5-Aminomethyl-6-phenyl-2-thiophen-2-yl-pyrimidin-4-ylamine,
5-Aminomethyl-6-(3-fluoro-phenyl)-2-phenyl-pyrimidin-4-ylamine,
5-Aminomethyl-2,6-diphenyl-pyrimidin-4-ylamine,
5-Aminomethyl-6-(4-methoxy-phenyl)-2-phenyl-pyrimidin-4-ylamine,
5-Aminomethyl-2-phenyl-6-thiophen-3-yl-pyrimidin-4-ylamine,
5-Aminomethyl-6-(3-methoxy-phenyl)-2-phenyl-pyrimidin-4-ylamine,
6-(2,4-Dichloro-phenyl)-5-methylaminomethyl-2-phenyl-pyrimidin-4-ylamine,
[5-Aminomethyl-6-(4-chloro-phenyl)-2-pyridin-3-yl-pyrimidin-4-yl]-methyl-amine,
5-Aminomethyl-6-benzo[1,3]dioxol-5-yl-2-(4-methoxy-phenyl)-pyrimidin-4-ylamine,
5-Aminomethyl-6-benzo[1,3]dioxol-5-yl-2-phenyl-pyrimidin-4-ylamine,
[5-Aminomethyl-6-(4-chloro-phenyl)-2-pyridin-3-yl-pyrimidin-4-yl]-isopropyl-amine,
(5-Aminomethyl-2,6-diphenyl-pyrimidin-4-yl)-methyl-amine,
and pharmaceutically acceptable salts thereof.

15. A pharmaceutical composition comprising a compound or a pharmaceutically acceptable salt thereof according to claim 1 and a pharmaceutically acceptable carrier.

16. A pharmaceutical composition comprising a compound of formula (I)

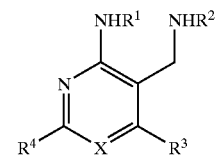

wherein
X is N;
$R^1$ and $R^2$ are independently hydrogen or lower alkyl;

$R^3$ is heterocyclyl; heterocyclyl mono-, di-, or tri-substituted, independently, by lower alkyl, lower alkoxy, perfluoro-lower alkyl, amino or halogen; aryl; or aryl mono-, di-, or tri-substituted, independently, by halogen, lower alkyl, lower alkoxy, amino or perfluoro-lower alkyl;

$R^4$ is methoxy;

$R^5$ is hydrogen or lower alkyl;

or a pharmaceutically acceptable salt thereof, and a pharmaceutically acceptable carrier.

17. A method for the treatment of diabetes or non-insulin dependent diabetes mellitus which comprises and administering a compound or a pharmaceutically acceptable salt thereof according to claim 1 to said patient in amount of from about 1–1000 mg per day.

18. The method according to claim 17, wherein said mount is from about 1–100 mg per day.

* * * * *

UNITED STATES PATENT AND TRADEMARK OFFICE
CERTIFICATE OF CORRECTION

PATENT NO. : 6,867,205 B2
DATED : March 15, 2005
INVENTOR(S) : Boehringer et al.

It is certified that error appears in the above-identified patent and that said Letters Patent is hereby corrected as shown below:

<u>Title page,</u>
Item [73], Assignee, "Hoffman-La Roche Inc." should be -- Hoffmann-La Roche Inc. --

Signed and Sealed this

Fourteenth Day of June, 2005

JON W. DUDAS
*Director of the United States Patent and Trademark Office*